(12) United States Patent
Shinton

(10) Patent No.: US 12,317,405 B2
(45) Date of Patent: May 27, 2025

(54) WAVEGUIDE FOR A PARTICLE ACCELERATOR

(71) Applicant: Elekta Limited, Crawley (GB)

(72) Inventor: Ian Shinton, Crawley (GB)

(73) Assignee: Elekta Limited, Crawley (GB)

(*) Notice: Subject to any disclaimer, the term of this patent is extended or adjusted under 35 U.S.C. 154(b) by 278 days.

(21) Appl. No.: 17/997,714

(22) PCT Filed: Apr. 30, 2021

(86) PCT No.: PCT/EP2021/061492
§ 371 (c)(1),
(2) Date: Nov. 1, 2022

(87) PCT Pub. No.: WO2021/219893
PCT Pub. Date: Nov. 4, 2021

(65) Prior Publication Data
US 2023/0232523 A1 Jul. 20, 2023

(30) Foreign Application Priority Data
May 1, 2020 (GB) .................................. 2006503

(51) Int. Cl.
*H05H 7/16* (2006.01)
*H01P 3/127* (2006.01)

(52) U.S. Cl.
CPC ............ *H05H 7/16* (2013.01); *H01P 3/127* (2013.01); *H05H 2277/11* (2013.01)

(58) Field of Classification Search
CPC ...... H05H 9/00; H05H 7/22; H05H 2007/225; H05H 9/02; H05H 9/044; H05H 7/16; H05H 7/18; H05H 7/20; H05H 9/048; H05H 2007/122; H05H 2277/11; H05H 7/001; H05H 7/12; H05H 9/045; A61N 2005/1087; A61N 5/1077; A61N 5/10; H01P 11/002; H01P 3/127; H01P 5/024; H01P 1/02; H01P 3/12; H01P 1/16; H01P 1/022; H01P 1/161; H01P 1/165; H01P 11/001; H01P 3/123
See application file for complete search history.

(56) References Cited

U.S. PATENT DOCUMENTS

2011/0285479 A1* 11/2011 Kang .................. H01P 3/12
333/242

OTHER PUBLICATIONS

Wilson et al., "Analysis of Rapidly Twisted Hollow Waveguides", IEEE Transactions on Microwave Theory and Techniques, Plenum, USA, vol. 56, No. 1, Jan. 1, 2009, pp. 130-139, XP011240652, ISSN: 0018-9480 (Year: 2009).*
"International Application Serial No. PCT/EP2021/061492, International Search Report dated Aug. 9, 2021", (Aug. 9, 2021), 6 pgs.
(Continued)

Primary Examiner — Lincoln D Donovan
Assistant Examiner — Tyler J Pereny
(74) Attorney, Agent, or Firm — Schwegman Lundberg & Woessner, P.A.

(57) ABSTRACT

Disclosed herein is a waveguide cell having a helical cavity. The waveguide cell has a central axis and a cavity having a transverse cross section whose rotational position about the central axis varies along the central axis. There is also disclosed a method a determining the shape of a waveguide cell.

14 Claims, 8 Drawing Sheets

(56) References Cited

OTHER PUBLICATIONS

"International Application Serial No. PCT/EP2021/061492, Written Opinion dated Aug. 9, 2021", (Aug. 9, 2021), 10 pgs.

Wilson, Joshua L, et al., "Analysis of rapidly twisted hollow waveguides", IEEE Transactions on Microwave Theory and Techniques 57.1, (2008), 130-139.

Wilson, Joshua L, et al., "Applications of twisted hollow waveguides as accelerating structures", IEEE Transactions on Nuclear Science 56.3, (2009), 1479-1486.

"European Application No. 21723222.2, Communication Pursuant to Article 94(3) dated Jan. 20, 2025", (Jan. 20, 2025), 8 pgs.

Wilson, Joshua L., "Twisted waveguides for particle accelerator applications", 2009 IEEE MTT-S International Microwave Symposium Digest, (2009), pp. 129-132.

\* cited by examiner 710 712

| | Known waveguide cell longitudinal cross section (1) | Helical cell transverse cross section (polar conversion of 1) | 3D Helical cell | Helical cell longitudinal cross section through the x/z plane | Helical cell longitudinal cross section through the y/z plane |
|---|---|---|---|---|---|
| Traditional pillbox shape cavity | 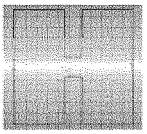 | 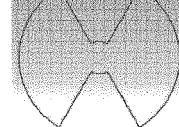 | 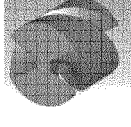 | 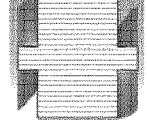 | 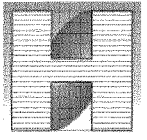 |
| Traditional pillbox shape cavity variant 1 | 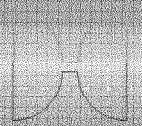 | 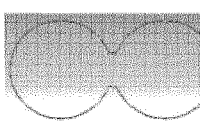 | 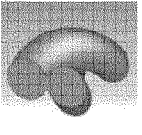 |  | 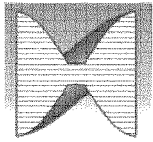 |
| Traditional pillbox shape cavity variant 2 | 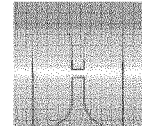 | 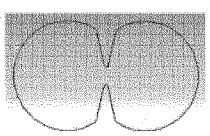 | 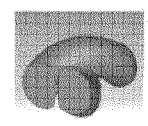 | 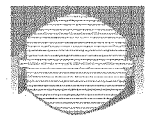 | 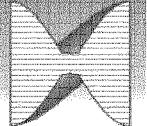 |
| Traditional pillbox shape cavity variant 3 | 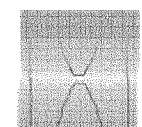 | 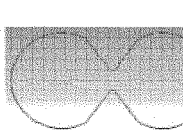 | 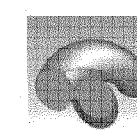 | 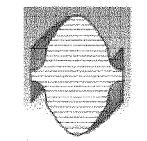 | 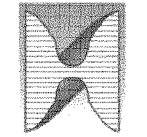 |
| Traditional pillbox shape cavity variant 4 | 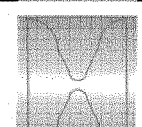 | 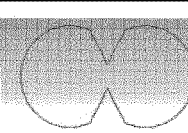 | 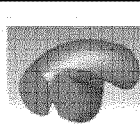 |  | 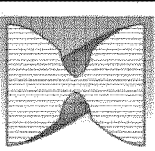 |
| Elliptical shape cavity |  | 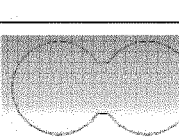 | 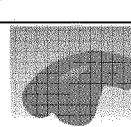 | 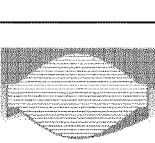 | 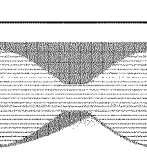 |
| Elliptical shape cavity variant 1 |  | 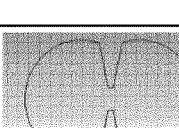 | 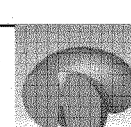 | 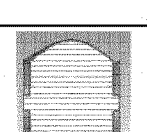 | 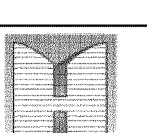 |
| Ichiro shape cavity |  | 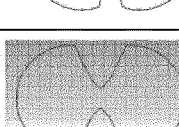 | 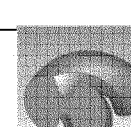 | 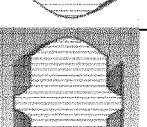 | 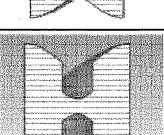 |
| Tesla shape cavity | 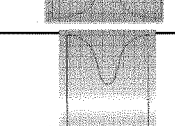 | 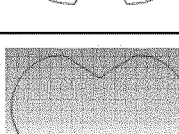 | 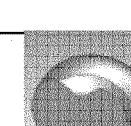 | 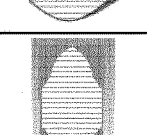 | 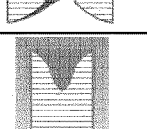 |

Figure 8

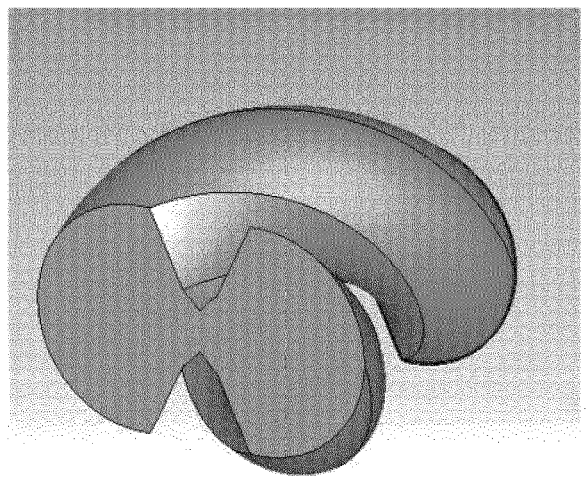
910
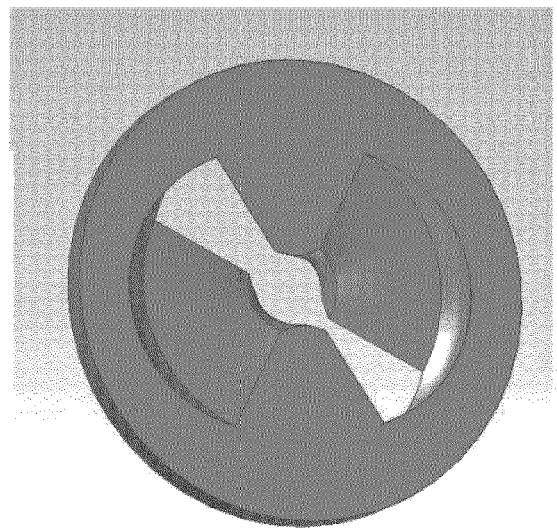
920
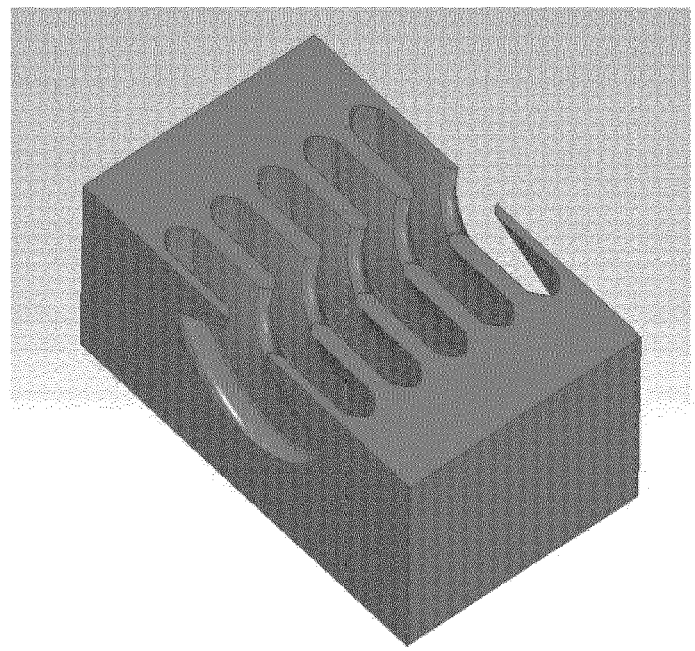
930
Figure 9

WAVEGUIDE FOR A PARTICLE ACCELERATOR

PRIORITY APPLICATIONS

This application is a U.S. National Stage Filing under 35 U.S.C. § 371 from International Application No. PCT/EP2021/061492, filed on Apr. 30, 2021, and published as WO2021/219893 on Nov. 4, 2021, which claims the benefit of priority to United Kingdom Application No. 2006503.3, filed on May 1, 2020; the benefit of priority of each of which is hereby claimed herein, and which applications and publication are hereby incorporated herein by reference in their entireties.

FIELD

The present disclosure relates to a waveguide, in particular a waveguide for a particle accelerator, to a method of designing a waveguide, and to a particle accelerator comprising a waveguide. The present disclosure also relates to a waveguide cell for a waveguide.

BACKGROUND

Particle accelerators are used to accelerate charged particles to high speeds.

Linear accelerators (especially those for medical use) accelerate charged particles such as electrons to relativistic speeds along an acceleration path through a waveguide. The waveguide has a number of resonant cavities located along the acceleration path. A radiofrequency (RF) electromagnetic wave (described throughout as RF energy, which refers to the energy in the electromagnetic wave) is applied to the waveguide which provides an oscillating electric field in each cavity. The field accelerates electrons.

The RF energy applied to the waveguide is used to accelerate the electrons along the acceleration path. Some factors limit the amount of RF energy which can be applied to a waveguide. For example, there is a point at which breakdown will occur.

SUMMARY

Aspects and features of the present invention are described in the accompanying claims.

According to a first aspect a helical waveguide cell is provided. A helical waveguide is comprised of helical waveguide cells, the helical waveguide cell comprising a helical cavity. A waveguide is comprised of resonant cavities, each resonant cavity can also be referred to as a waveguide cell. There is provided a waveguide comprising a helical cavity, and a waveguide cell comprising a helical cavity.

Optionally, the waveguide cell further comprises a central axis and a cavity having a transverse cross section whose rotational position about the axis varies along the axis. The transverse cross section is non-circular. The transverse cross section may be referred to as a fixed transverse cross section given that the cross sectional shape does not change along the length of the cell, but the rotational position of the cross sectional shape does change along the length of the cell. The transverse cross section of the waveguide cell is a constant shape along the length of the cell, only its rotational position changes along the length of the cell. Each transverse cross sections of a helical waveguide cell of the present invention have rotationally symmetry with each other. The central axis of the helical waveguide cell is the acceleration axis for electrons to travel along and can be labelled by the z axis. The length of a waveguide cell is the distance along the acceleration axis for one cell. The transverse cross section is used to define the cross section in a plane orthogonal to the central axis which is labelled the x/y plane (if z is defined as the central axis). The cavity may comprise a non-circular transverse cross section helically rotated around the central axis along the axis. The cavity may be referred to as a helical cavity.

Optionally, the waveguide cell further comprises its transverse cross section continuously helically rotated along the length of the cell. The rotational position of the transverse cross sectional shape changes along the length of the cell, the change in rotational position is continuous. Each unit of movement along the longitudinal length of the cell (in the z direction) corresponds to a rotation of the transverse cross section of the cell around the central axis. The rotation rate (amount of rotation per length) may or may not be constant. Optionally, the rotation rate is fixed/constant.

Optionally the transverse cross section is helically rotated along the length of the cell through 180 degrees. That is, the rotational position of the transverse cross section changes by 180 degrees long the length of the cell. The total twist angle of the transverse cross section is 180 degrees.

Optionally, the transverse cross section is rotated at a fixed rotation rate along the length of the cell. The fixed rotation rate along the length of the cell can be termed the twist rate, the twist rate may be defined in units of rad/m or degrees/m.

Optionally the twist rate is $\pi/L$, where L is the length of one cavity. A constant twist rate of $\pi/L$ along the length of the cell results in 180 degrees rotation of the transverse cross section along the length of the cell.

The length of one cavity L remains constant as it is fixed in the conversation between a conventional cavity it's helical cavity counterpart. The length of cell L is a periodic length and the length L may be repeated multiple times to form a waveguide comprising a series of cells. The length of a waveguide cell is the distance along the acceleration axis for one cell or cavity.

Optionally, the waveguide cell further comprises a longitudinal cross section in a first plane and a longitudinal cross section in a second plane at an angle to the first plane which are the same shape out of phase relative to each other.

Optionally, the waveguide cell further comprises a longitudinal cross section at a first angle and a longitudinal cross section of the waveguide cell at a second angle orthogonal to the first angle which are 180 degrees out of phase relative to each other. In other words, the longitudinal cross section in a first plane and in a second plane orthogonal to the first plane is the same shape translated by half of the cycle. A longitudinal cross section can be in any plane containing the central axis (the z axis). That is, a longitudinal cross section might be the y/z or the x/z plane but may also another plane taken at any angle around the z axis. The x/z plane is equivalent to a plane taken at a 0 or 180 degree angle around the z axis. The y/z plane is equivalent to a plane taken at a 90 or 270 degree angle around the z axis. A longitudinal cross section at a first angle around the z axis refers to taking a 2D plane from a 3D cavity/waveguide cell at the first angle. This may be referred to as a longitudinal cross section in a first plane. A longitudinal cross section at a second angle around the z axis which refers to taking a 2D plane from a 3D cavity/waveguide cell at the second angle. This may be referred to as a longitudinal axis in a second plane. The two cross sections at the two angles define different unit cells of the same periodic structure, the unit cells shifted by one-half cycle relative to the other and so are 180 degrees out of phase relative to each other. The two cross section unit cells therefore have a constant area contained within the shape they define as well as the same periodic length, L.

Optionally, the helical cavity has a known (non-helical) cavity counterpart produced via known techniques. The helical cavity is derived from the shape of the known counterpart cavity. The transverse cross section of the helical cavity is the polar coordinates conversion of the cartesian longitudinal cross section of the counterpart known cavity. Similarly, helical waveguides have a counterpart known (non helical) waveguide. In some planes, the longitudinal cross section of the helical waveguide (cell) has the shape of the longitudinal cross section of the counterpart waveguide (cell).

Optionally, the waveguide cell further comprises a fixed non-circular transverse cross section derived from a 2D shape having an iris and an equator, and wherein the longitudinal cross section of the cell viewed at a first angle is an iris to iris unit cell, and viewed at a second angle orthogonal to the first is an equator to equator unit cell. An equator-to-equator unit cell starts at a wide point of the cavity (equator) then narrows at the narrowest point (iris) and then finishes at a wide point (equator). A cavity unit cell may also be defined as an iris-to-iris which starts at a narrow point (iris), then widens to the widest part (equator), then finishes at a narrow point (iris). An equator-to-equator and iris-to-iris unit cell are 180 degrees out of phase relative to each other.

Optionally, the waveguide cell further comprises a non-circular transverse cross section helically rotated along the length of the cell through 180 degrees. Helical rotation is where a polar 2D cross section is extruded back in the z axis of the Cartesian coordinate system with a certain twist rate. The twist rate may be UTE Over a length of L the two-dimensional polar shape is continuously twisted by 180 degrees to generate a 3D shape. The two-dimensional polar cross section is progressively rotated in a continuous fashion around the z axis along the length of the axis, to 'sweep out' the shape of a cavity. The two-dimensional polar cross section is the transverse cross section of the waveguide cell. The twist rate $\pi/L$ is a fixed rotation rate along the length of the cell L, the twist rate may be defined in units of rad/m or degrees/m. The length of cell L is a periodic length and the length L may be repeated multiple times to form a waveguide comprising a series of cells.

According to an aspect there is provided a waveguide comprising a series of cells. The waveguide may comprise helical resonant cavities, each resonant cavity can also be referred to as a waveguide cell.

Optionally, the waveguide further comprises a longitudinal cross section in a first plane at a first angle with a periodic structure, and wherein the longitudinal cross section in a second plane orthogonal to the first plane has the periodic structure 180 degrees out of phase relative to the first plane. The two cross sections at the two angles define different bounds of the same periodic structure, the cross sections are shifted by one-half cycle relative to the other and so are 180 degrees out of phase relative to each other.

According to an aspect there is provided a method of determining a 3D shape of a waveguide cell, the method comprising: identifying a Cartesian 2D cross section; helically rotating the cross section around the central axis along the length of the cell to generate a 3D shape; and outputting the 3D shape. The Cartesian 2D cross section comprises an equator and an iris. The Cartesian 2D cross section is a longitudinal cross section of a cavity, such as a cross section of a standard cavity made using known techniques. The shape may be taken or derived from a table of known cavity shapes. The 3D shape generated can be considered a "helical cavity" since the 3D shape defines a resonant cavity and is produced via helical rotation around the z axis.

Optionally, the waveguide cell has a length L and identifying a 2D cross section comprises: identifying a Cartesian 2D cross section of a cell in Cartesian coordinates; and generating a polar 2D cross section in polar coordinates by converting the 2D Cartesian cross section into polar coordinates, the θ direction being defined as between 0 and $L/2\pi$; and wherein: helically rotating the polar 2D cross section around the central axis along the length of the cell to generate a 3D shape comprises: extruding the 2D polar coordinates shape back in the z axis of the Cartesian coordinate system with a twist rate of $\pi/L$. The periodic length of the cell L is fixed and the geometry of the longitudinal cross section is converted from Cartesian coordinates to a cylindrical coordinate system in the r and a plane.

Optionally, identifying a 2D cross section comprises: identifying a periodic Cartesian 2D cross section of a cell wherein the periodic Cartesian 2D cross section defines a periodic function f(z); and wherein helically rotating the cross section around the central axis along the length of the cell to generate a 3D shape comprises: transforming the periodic function f(z) into a new function F(θ) in a helical coordinate system, the z values are converted by a twist rate $\pi/L$ and the value of a ranges from 0 to $L/2\pi$. The helical rotation is achieved by mapping the cartesian coordinate system onto a helical coordinate system. The periodic function f(z) is representative of the conventional cavity shape along the acceleration axis (the central axis), the z direction. The function f(z) is periodic in terms of the cavity/cell length L along the z axis. The function f(z) may define a conventional longitudinal cross section across a plurality of cells. The cartesian function f(z) is transformed into a new function F(θ) in the helical coordinate system, the z values are converted in terms of a twist rate $\pi/L$ and hence the value of a ranges from 0 to $L/2\pi$. The values of θ are defined by the value of the f(z) function is as the values are converted in the F(θ) frame.

Optionally, the method further comprises the Cartesian 2D cross section of the cell comprising an equator and an iris, and wherein the longitudinal cross section of the cell viewed at a first angle is an iris to iris unit cell, and viewed at a second angle orthogonal to the first is an equator to equator unit cell. An equator-to-equator and iris-to-iris unit cell are 180 degrees out of phase relative to each other.

Optionally, the method further comprises simulating an electric field created upon the application of radiofrequency energy to a waveguide comprising cells having the 3D shape using Maxwell solving computational software. Radiofrequency (RF) electromagnetic waves can be described as RF energy, which refers to the energy in the electromagnetic wave. The radiofrequency energy can be simulated into the waveguide to provides an oscillating electric field in each cavity.

Optionally, the method further comprises identifying the maximum field. The maximum field may be the maximum electric, magnetic field or both. The maximum field may be found for the surface of the cavity.

Optionally, the method further comprises simulating an electric field created upon the application of radiofrequency energy to a waveguide comprising a cavity having the shape of the 2D Cartesian cross section swept out around the central axis; identifying the maximum surface field in the simulation; comparing the maximum surface field to the first maximum field; and using computational software to solve Maxwell's equations. A cavity having the shape of the 2D Cartesian cross section swept out around the central axis is a cavity according to known techniques, wherein there is no helical rotation. Comparing the maximum surface field to the first maximum field involves comparing the maximum field of the cavity produced using known techniques with its helical counterpart.

Optionally, the method further comprises a Cartesian 2D cross section which is the longitudinal cross section of a known cavity shape and wherein the known cavity shape comprises one of: a pillbox shape, an elliptical shape, an Ichiro shape or a Tesla shape. Standard waveguides known in the art may comprise standard cavity shapes such as the pillbox shape, elliptical shape, Ichiro shape or a Tesla shape.

Optionally, the method further comprises manufacturing a waveguide having the 3D shape. The waveguide may comprise helical resonant cavities, each resonant cavity can also be referred to as a waveguide cell.

According to an aspect there is provided a method of determining the shape of a 3D waveguide cell having a length L, comprising: identifying a periodic Cartesian 2D cross section of a cell wherein the periodic Cartesian 2D cross section defines a periodic function $f(z)$; transforming the periodic function $f(z)$ into a new function $F(\theta)$ in a helical coordinate system, wherein the z values are converted by a twist rate $\pi/L$ and the value of $\theta$ ranges from 0 to $L/2\pi$; and outputting the shape.

According to an aspect there is provided a waveguide manufactured by the method of another aspect.

According to an aspect there is provided a waveguide cell illustrated in any of FIGS. 6 to 9 of the application.

According to an aspect there is provided a particle accelerator comprising the waveguide described above. According to an aspect there is provided a linear accelerator comprising the waveguide described above. According to an aspect there is provided a radiotherapy device comprising a linear accelerator having a waveguide described above.

According to an aspect there is provided a waveguide cell having a central axis and a cavity having a transverse cross section whose rotational position about the central axis varies along the central axis.

BRIEF DESCRIPTION OF THE DRAWINGS

Specific embodiments are described below by way of example only and with reference to the accompanying drawings in which:

FIG. 8 illustrates a number of cavities according to the present disclosure; and FIG. 9 illustrates manufacture of a waveguide comprising helical cavities according to the present disclosure.

SPECIFIC DESCRIPTION OF CERTAIN EXAMPLE EMBODIMENTS

The present invention provides a waveguide cell shape, termed "helical cells" or "helical cavities" and a method of generating a helical cell starting from a cavity shape known in the art. A helical cavity is a resonant cavity, the helical shape of the cavity is generated via a continuous rotation of a 2D cross section extruded into the z axis where the rotation rate can be considered a constant twist rate (rad/m) and where the 2D cross section is derived from the known cavity shape. The helical waveguide of the present invention has field cancelling properties. When a helical cavity is compared to its known cavity counterpart, the helical cavity may reduce surface field, reduce surface field at the irises, prevent RF breakdown at the cavity surface and improve the accelerating gradient of beam generation.

FIG. 1

In radiotherapy, radiation is delivered to a patient to damage unhealthy tissue and cells, such as cancerous tumours. A treatment plan is created to determine the amount of radiation to be applied to the patient (the dose). It is desirable to deliver the required radiation to the patient in as short time as possible for a number of reasons. A faster radiation treatment will reduce the overall treatment time, hence reducing discomfort and inconvenience to the patient. It will also increase the number of patients who can be treated per day.

One way of decreasing the treatment time is to increase the dose rate (amount of radiation applied per second). It is desirable to decrease patient treatment time, in order to make the experience as comfortable as possible for the patient. Additionally, the patient will move during the treatment, and this movement can be problematic and difficult to account for during treatment. Decreasing treatment time can also minimise the effects of the patient's movement on the treatment.

Figure 1:
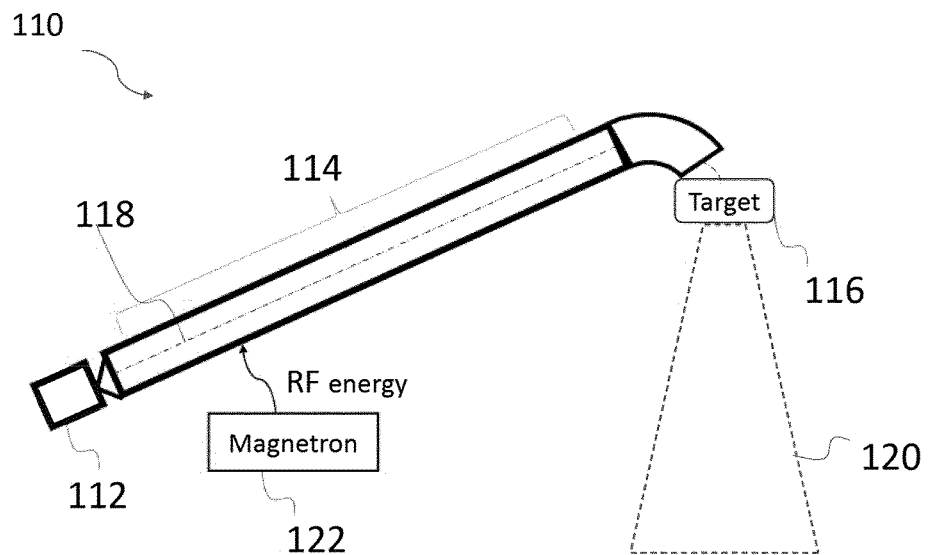
FIG. 1 illustrates a linear accelerator for use in radiotherapy.

A high-level overview of a linear accelerator is illustrated in FIG. 1. The linear accelerator 110 includes a source of electrons 112, a waveguide 114, and a target 116. Electrons are emitted from the electron gun and accelerated through the waveguide along an acceleration path 118 which is coincident with the central axis of the waveguide. The electron beam is bent using magnets and strikes the target 116, to produce an x-ray beam 120. The x-ray beam 120 is used to treat a patient.

The source of radiofrequency waves 122, such as a magnetron, produces radiofrequency (RF) waves. The source of radiofrequency waves is coupled to the waveguide, and is configured to pulse radiofrequency waves into the waveguide.

The source of electrons 112 may be an electron gun. The source of electrons is configured to inject electrons into the waveguide 114. The waveguide 114 comprises a plurality of interconnected acceleration cavities (not shown) forming a channel through which the electron beam passes. The injection of electrons into the waveguide 114 is synchronised with the pumping of the radiofrequency waves into the waveguide 114.

The design and operation of the radiofrequency wave source 122, electron source 112 and the waveguide 114 is such that the radiofrequency waves accelerate the electrons to very high energies as they propagate through the waveguide 114 down the acceleration path 118. The waveguide is designed in order that a suitable electric field pattern is produced which accelerates electrons propagating through the waveguide 114.

The waveguide and linear accelerator are described in FIG. 1 for use in a radiotherapy device. However the waveguide in the present disclosure can be used in a particle accelerator for systems other than radiotherapy devices. The disclosure is not limited solely to waveguides for particle accelerators for radiotherapy devices.

Figure 2:
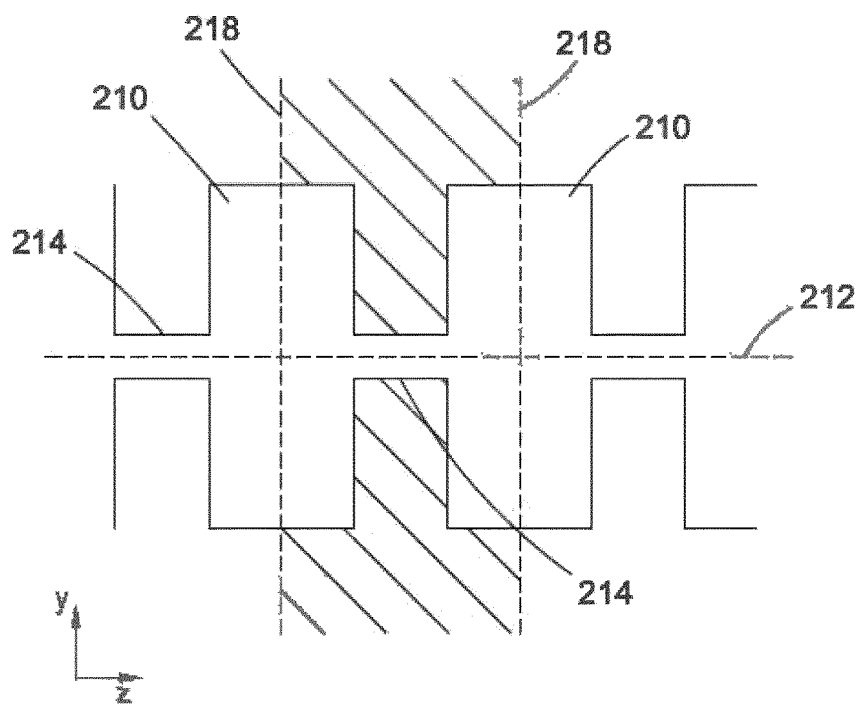
FIG. 2 illustrates a portion of waveguide for a particle accelerator.

A waveguide for use in a particle accelerator is illustrated in FIG. 2. This is a cross section view along the longitudinal axis of the waveguide, or a "longitudinal cross section". This waveguide can be used in a linear accelerator as shown in FIG. 1, but also could be used in other accelerators (e.g. a curved accelerator such as a cyclotron or a synchrotron). The below examples and discussion related to the acceleration of electrons, but the waveguide can be used in the acceleration of any charged particle and therefore in any charged particle accelerator. For example, protons, positrons and ions can be accelerated using the techniques described herein.

FIG. 2 Brief Description of a Known Waveguide

FIG. 2 illustrates a portion of a known waveguide. A waveguide is a periodic structure, the waveguide comprising of waveguide cells, the cells having a cavity. In other words a waveguide is comprised of resonant cavities, each resonant cavity can also be referred to as a waveguide cell. Two cavities 210 of a series of connected cavities are shown. The cavities are each connected along a central axis 212 by irises 214. Only two complete cavities are illustrated in FIG. 2, although a typical waveguide will have more. The precise number will vary, dependent on the design criteria of the accelerator. Each cavity is defined in the form of a recess within a surrounding shell of a conductive material, usually copper. The central axis may be referred to herein as the acceleration axis, the centre axis, or the z axis.

In the following description, the term "longitudinal cross section" is used to define the cross section in any plane through the central axis. The "transverse cross section" is used to define the cross section in a plane orthogonal to the central axis. A longitudinal centre of an object is the halfway down the object's longitudinal axis. For example, the longitudinal centre of a cavity is the plane half way along the central axis of that cavity. The longitudinal centre may also be referred to as the equator of the cavity. In the following description, the z axis is defined as the centre or central axis. A longitudinal cross section may therefore be described the y/z or the x/z plane. The longitudinal cross section is taken in a plane containing the central axis (the z axis). The transverse cross section is described by the x/y plane, a plane orthogonal to the z axis.

A longitudinal cross section can be in any plane containing the central axis (the z axis). That is, a longitudinal cross section might be the y/z or the x/z plane but may also another plane taken at any angle around the z axis. The x/z plane is equivalent to a plane taken at a 0 or 180 degree angle around the z axis. For example, this could be a longitudinal cross section taken looking 'side on'. The y/z plane is equivalent to a plane taken at a 90 or 270 degree angle around the z axis. For example, this could be a longitudinal cross section taken looking from above or below the waveguide.

Each cavity 210 has an iris 214 connecting to the preceding cavity in the sequence, and an iris 214 connecting to the next cell in the sequence. The irises and cavities are centred on the central axis. In use, the central axis defines the electron acceleration path, the path along which electrons travel when being accelerated though the waveguide. Generally, cavities and irises are axisymmetrical around the central axis, forming a rounded toroid, i.e. the three-dimensional shape created by sweeping a two-dimensional shape around the axis. In some waveguides a "nose cone" is formed on each end of the irises, lengthening the iris along the central axis to protrude into the cavity. However, some waveguides such as the one shown in FIG. 2 do not include a nose cone.

The cavities are manufactured by welding segments of conductive material together at joining portions. The joining portions of the segments are typically in the "equator" of the cavity, the equator is the longitudinal centre of the cavity. The equator is usually the widest point of the cavity, where the width refers to the y axis. Additionally, the plane at the equator is a plane of symmetry. Each cavity 210 is made from two separate segments adjoining at the central equator. Each segment has two equators 218, which define the leftmost and rightmost edges of the segment. A segment is illustrated on FIG. 2 as the shaded portion. Adjoining segments create a unit cell, which is repeated to form a waveguide. The shaded segment is an example of an equator-to-equator unit cell or a wide-narrow-wide structure (WNW). A WNW shape starts at a wide point (equator 218), then narrows at the iris 214, then finishes at a wide point (equator 218). A cavity unit cell may also be defined as an iris-to-iris or narrow-wide-narrow structure (NWN). A NWN cavity shape starts at a narrow point (an iris), then widens to the equator, then finishes at a narrow point (an iris). Typically a cavity is described as having two irises. Some cavities are manufactured using segments with joining portions elsewhere in the waveguide.

A waveguide is a periodic structure, the waveguide comprising of waveguide cells, the cells having a cavity. A cell refers to a section of waveguide with a cavity in conductive material, i.e. to the portion of a waveguide having a cavity. The structure of the waveguide varies with a particular frequency or periodicity along its length, for example, the width of the waveguide along its length varies between iris features and equator features, Accordingly, a particular phase of this structural variation frequency, or periodicity, can be defined at a particular point along the length of the waveguide. An iris-to-iris and an equator-to-equator unit cell of a cavity can be considered as being perfectly out of phase with each other. The iris-to-iris and equator-to-equator unit cells define two separate starting points from which to define the cavity shape. The cell can be described as a periodic structure. The equator is half way between the irises, and in this way the iris-to-iris and equator-to-equator unit cells are shifted by one-half cycle relative to the other. In terms of a periodic difference between the forms, the iris-to-iris and equator-to-equator could be considered as 180 degrees out of phase with each other. The iris-to-iris and equator-to-equator unit cells therefore have a constant area contained within the shape they define as well as the same periodic length, L. There are an infinite number of alternative unit cells which can be used to describe the same cavity shape, each unit cell using a different starting point along the shape. Iris-to-iris and equator-to-equator unit cells are the most commonly used unit cells and will be referred to herein.

Figure 3:
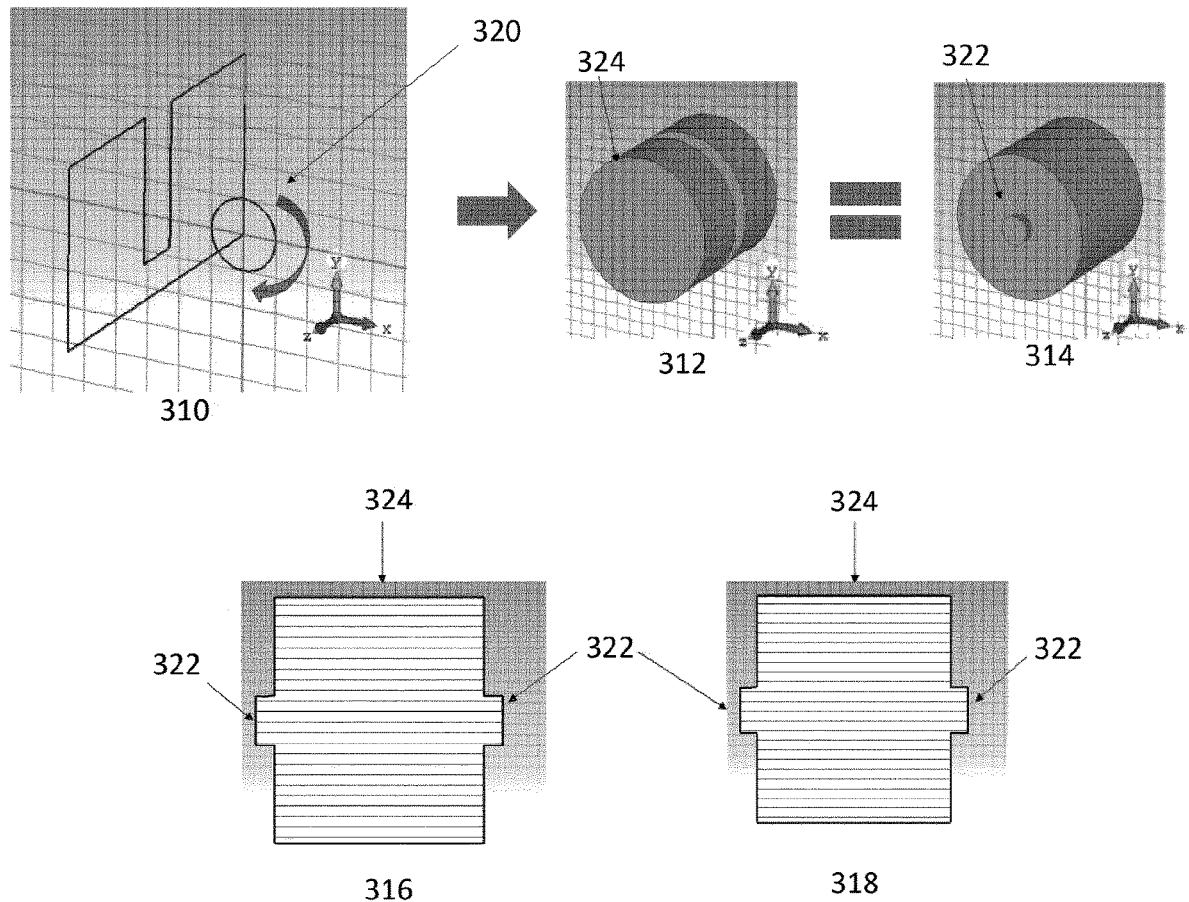
FIG. 3 illustrates conventional generation of a waveguide cavity shape.

The changing electromagnetic field introduced in the waveguide over time through the application of radiofrequency waves to a model of the waveguide can be simulated. In turn, this can be used to simulate the effect of the electromagnetic field on an electron, or multiple electrons, injected at one end of the waveguide. The acceleration of electrons along the acceleration path, the speeds of the electron at the far end of the waveguide (the opposing end to the electron gun) and, as some electrons are deflected sideways off the acceleration path, the proportion of electrons reaching the far end of the waveguide can also be determined. In medical applications, this information can be used to determine the dose of radiation created by a waveguide. The electromagnetic field simulation is typically determined by numerical methods, for example, numerical computational software able to solve Maxwell's equations.
FIG. 3—Brief Description of how a Known Waveguide Shape is Determined FIG. 3 shows conventional generation of a waveguide with a "pill-box" cavity shape according to known techniques. Although FIG. 3 is illustrated for a pill-box shape, the method is equally applied to any known standard cavity shape. The waveguide is comprised of repeated iris-to-iris unit cells 314. First, a longitudinal profile of the cavity unit cell is determined, 310, the longitudinal profile is a two-dimensional shape which can be used to define the shape of a waveguide. The longitudinal profile is in a plane intersecting the central (acceleration) axis; for example the x/z or the y/z plane. The two-dimensional shape is the profile of the cavity bound by the acceleration axis. That is, the acceleration axis forms an outer-most lower edge of the two-dimensional shape.

In the example in FIG. 3 the longitudinal profile 310 defines a conventional pill-box cavity for the equator-to-equator unit cell. As the skilled person will appreciate, there are numerous known cavity shapes with corresponding longitudinal profiles. The two-dimensional longitudinal profile 310 is then swept around the z axis to form a hollow three-dimensional shape 312, representative of a three-dimensional cavity defined as an equator-to-equator unit cell. The three-dimensional shape 312 is therefore axisymmetric or rotationally symmetric about the central axis (z axis). For any cross-section of the waveguide taken through an x/y plane, the radially outermost surface of the internal waveguide cavity will form a circle.

The three-dimensional cavity in equator-to-equator form 312 may be manufactured as a segment (such as the shaded segment in FIG. 2) and a series of segments aligned to produce a series of iris-to-iris cavities. A three-dimensional cell in equator-to-equator form 312 can be processed into its iris-to-iris form 314. The three-dimensional cavity in iris-to-iris form 314 may also be found by using a two-dimensional longitudinal profile defined for a cavity in iris-to-iris form. The three-dimensional shape in either equator-to-equator 312 or iris-to-iris form 314 may be repeated adjacently to form a waveguide shape. Equators 324 and irises 322 are shown in FIG. 3.

In any transverse cross-section of the waveguide or three-dimensional shape 312, 314 is taken through an x/y plane, the radially outermost surface of the internal waveguide cavity will form a circle. The cross section of the channel formed by the cavities and irises across its width at any one point is circular or made from a number of circles. The waveguide is toroidal. It will be appreciated that known waveguides as depicted in FIGS. 2 and 3 have an infinite order of rotational symmetry about the central axis (z axis). To aid understanding, it is noted that the simplest conceivable shape which also has an infinite order of rotational symmetry is a circle. Any shape with an infinite order of rotational symmetry about a point consists of a circle or a plurality of circles with their centres located on the point.

The axisymmetry is also evident in in the longitudinal cross section of the cavity. A longitudinal cross section in any plane containing the central axis is the same regardless of the angle of the plane. That is, the longitudinal cross section of the cavity does not change upon rotation around the central axis. The longitudinal cross section in the y/z plane is the same as the longitudinal cross section in the x/z plane, and the same as in any plane therebetween.

If the three-dimensional shape 314 is viewed at a longitudinal cross section at a first angle around the z axis, nominally 0 degree rotation around the z axis, an iris-to-iris unit RF cell is obtained (316). If the three-dimensional shape is viewed with a longitudinal cross section at a second angle around the z axis, the second angle orthogonal to the first, being at 90 degree rotation with respect to the z axis, an iris-to-iris unit RF cell is obtained (318). The cross-section at the first angle and the second angle is the same. Indeed, the longitudinal cross section taken at any angle with respect to the z axis is the same. Equivalently, if a cross section through the three-dimensional shape 314 is taken through the x/z plane at a central point (i.e. at y=0) the cross section 316 is produced. If a cross section through the three-dimensional shape 314 is taken through the y/z plane at a central point (i.e. at x=0) the cross section 318 is produced. Due to the symmetry about the central axis (z axis), the two cross-sections through the y/z and x/z planes are identical. Accordingly there is rotational symmetry around the z axis.

Cross sections 316, 318 are analogous to the cavity cross section shown in FIG. 2. FIG. 2 represents a conventional "pill-box" cavity shape, FIG. 3 also represents a conventional pill-box cavity shape. The equators 324 and irises 322 are marked for the cross sections 316 and 318.

Simulation and Breakdown

For simulation, typically software is used in which two-dimensional measurements of a waveguide are entered into the software, i.e. a longitudinal profile of the cavity unit cell such as 310, to create a 2D axisymmetric framework for a full 3D model. The electric field over time generated by the application of radiofrequency waves to the waveguide is simulated based on the full 3D model of the waveguide. A waveguide can then be built based on this model of the waveguide. Alternatively, the above process can be used to model the electric field of an existing waveguide, through inputting the dimensions of that waveguide. Typically these simulations have always been performed taking into account only two-dimensions. Meaning traditionally, waveguides and the cavities/irises within waveguides are initially manufactured to be axisymmetric (formed through sweeping a two-dimensional shape around the central axis).

When RF energy is applied to a waveguide, an electric field is created in the waveguide; both in the material of the waveguide and in the cavity. The electric field is not uniform across the waveguide. Surface electric fields are formed on the surface of the cavity. Areas with a high surface electric field are more likely to cause electrical breakdown.

Breakdown is caused by a combination of large surface electric and magnetic fields and is a complex phenomenon dependent on many conditional factors in addition to the driving fields. Factors include field emissions, multipacting, gas breakdown and surface heating. During breakdown the number of electrons reaching the target is typically reduced. In some instances, the number of electrons reaching the target is zeroed. Whether RF breakdown occurs can be somewhat predicted by empirically derived formulas such as the Kilpatrick breakdown limit for conducting accelerating structures:

$$E_{Smax} \sim 195\sqrt{f} \qquad [1]$$

where $E_{Smax}$ is the maximum surface field (MV/m) and f is the frequency of the RF waves (GHz). If the surface field is greater than the Kilpatrick breakdown limit, there is high probability of RF breakdown in this location. The Kilpatrick limit provides an estimate since the mechanism of RF breakdown does depends on many conditional factors.

Therefore waveguides for radiotherapy are designed for stability to avoid breakdown, this is a trade-off with wanting as high fields as possible within the accelerating structure to provide either:

1. High dose rate (from over beamloading the transfer of energy from the RF field to the beam itself, by having more input beam current put into the guide (from the particle source) and raising the RF field to accelerate the additional particles to the same energy and hence increasing the final dose rate)
2. High energy (from under beamloading the transfer of energy from the RF field to the beam itself by having more field present to increase the overall gradient of the accelerating field that is seen by the particles and accelerate them to a higher final energy).

Hence it is desirable to increase the RF energy which can be applied to the cell before breakdown occurs for either of the above cases.

Figure 4A:
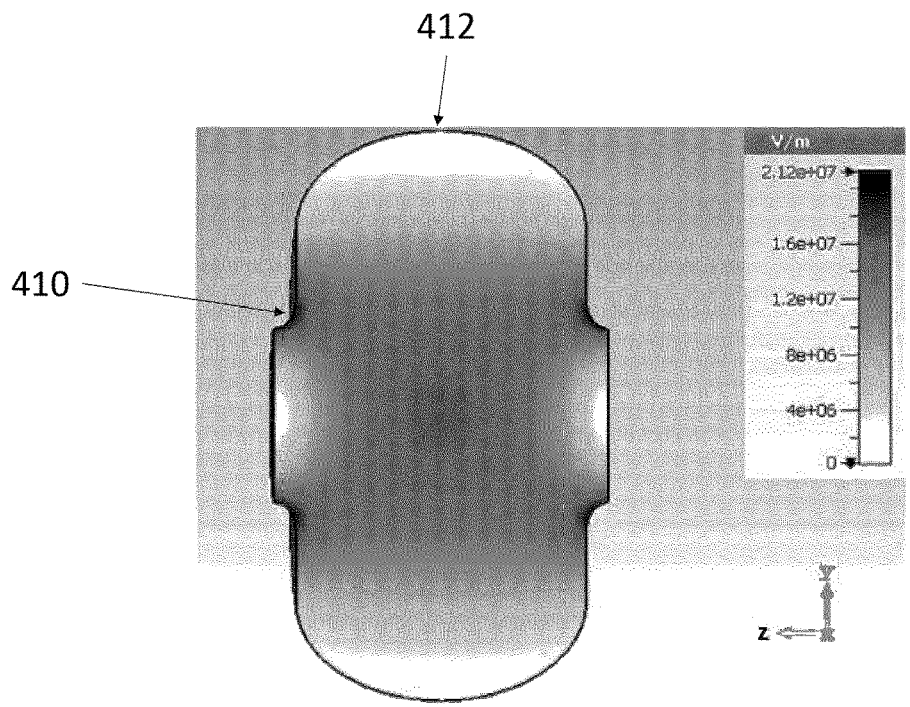
FIGS. 4a and 4b illustrate a field map formed through the application of RF energy to a known waveguide.
Figure 4B:
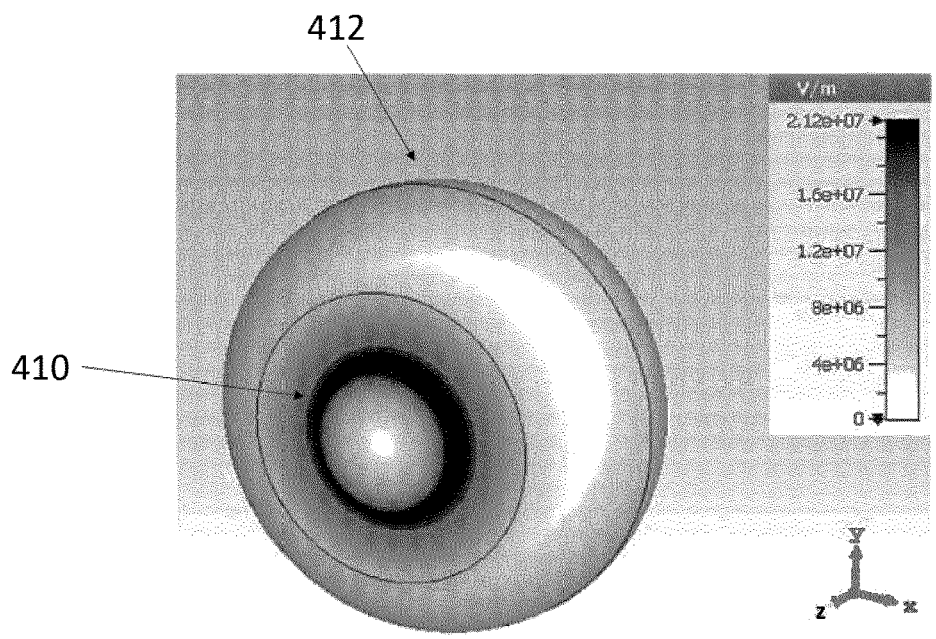

A field map of the intensity of an electric field created in a cavity when RF energy is applied to a known, axisymmetric waveguide (such as the waveguide of FIG. 2) is illustrated in FIGS. 4a and 4b. The simulated input RF frequency was calculated at 1.3 GHz.

FIG. 4a shows a longitudinal cross section of waveguide cavity (a cross section taken along the z axis), and FIG. 4b shows a perspective view of a whole cavity. The shape of the cavity is a conventional "Ichiro" shape.

The intensity is illustrated as a greyscale colour map, with the most intense (i.e. highest density) electric field coloured black, the least intense (i.e. lowest density) field coloured white, and the field intensity therebetween shown in greyscale. The highest field (shown in black) is on the surface of the iris and on the nose cone, as indicated by reference numeral 410. There is also high field in the centre of the cavity along the acceleration path. The lowest field (shown in white) is through the centre of the iris along the acceleration path, and at the radial edge of the cavity around the centre plane, indicated by reference numeral 412.

The point of peak surface field (i.e. this highest electric field) is on the surface of the iris. This is also the point of the surface of the cavity which is closest to the acceleration path. The high field means that breakdown may occur in this location.

The present disclosure provides a waveguide and method of manufacturing a waveguide with a reduced likelihood of breakdown.

In the present disclosure, a helical cavity is provided to reduce the surface field and prevent RF breakdown. A waveguide comprising a cavity with a helical shape can reduce the maximum surface field. An example method for determining a helical shape of a waveguide cavity is provided below.

As explained above, a typical cavity is generated using a shape in a two-dimensional Cartesian coordinate system (a longitudinal profile) and sweeping the two-dimensional shape around the central axis, the z axis in a cylindrical coordinate system. This creates an axisymmetric waveguide and is represented in FIG. 3. According to the present disclosure, a new cavity shape is generated by reconsidering the two-dimensional shape which is swept around the central axis and how the sweep of a two-dimensional shape around the central axis is conducted.

Figure 5:
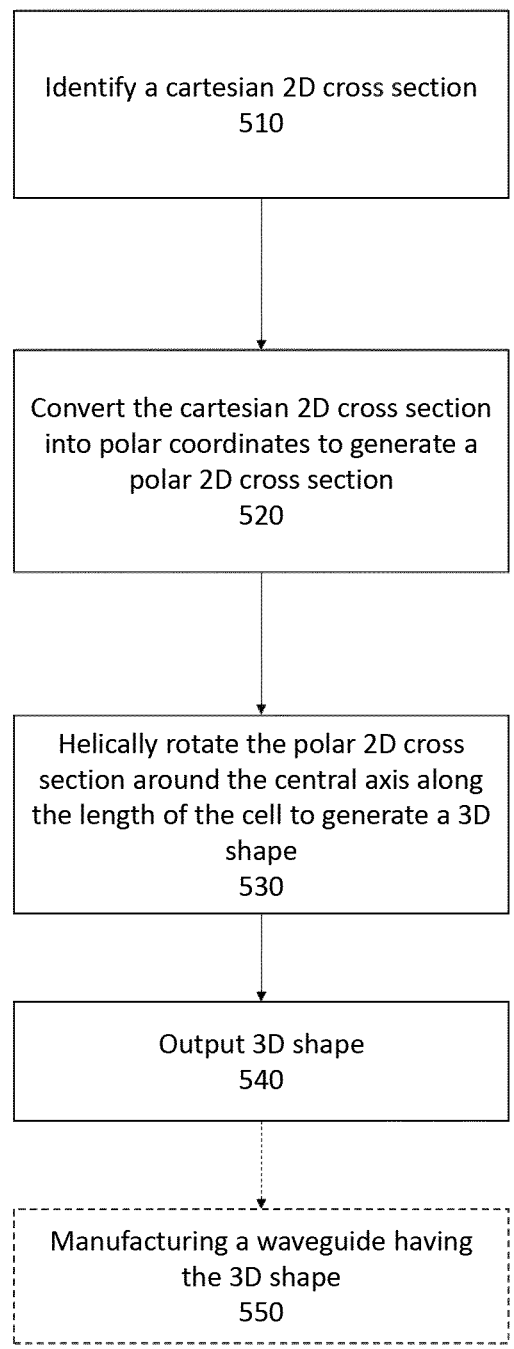
FIG. 5 illustrates a method of determining the shape of a waveguide according to the present disclosure.
Figure 6:
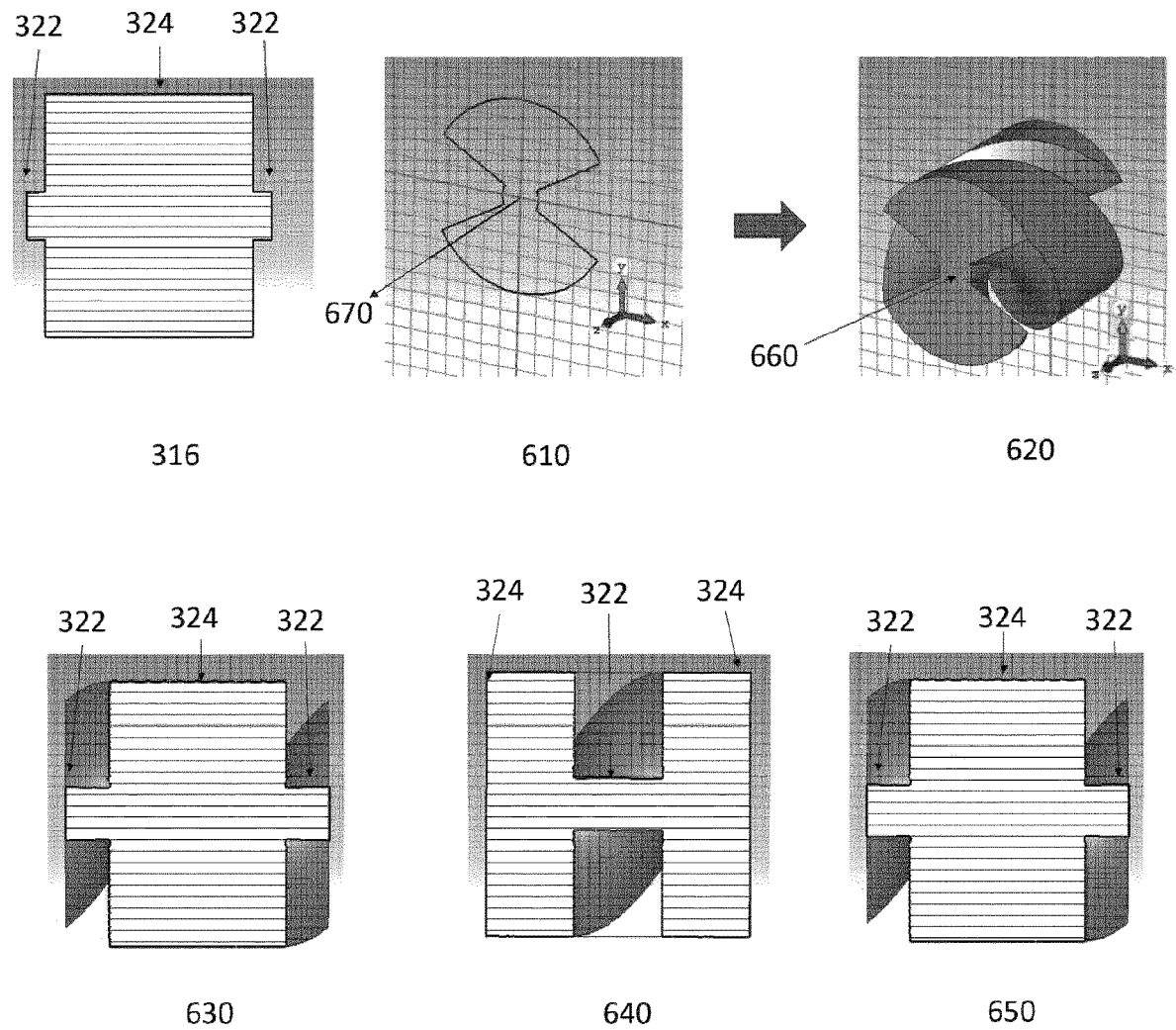
FIG. 6 illustrates a helical cavity according to the present disclosure.

Reference is now made to FIG. 5 which depicts a method according to the present disclosure. Reference is also made to FIG. 6 which depicts a helical cavity of the present disclosure.

FIG. 5—Method of Creating Helical Cavity

In a first step, a shape of a transverse cross section of a waveguide to be helically rotated around the central axis is identified. One such method of doing this is given in steps 510 to 520.

The method begins at step 510. At step 510, a two-dimensional shape of a cell in Cartesian coordinates is identified. The Cartesian two-dimensional cross section comprises an equator and an iris. The shape is a longitudinal cross section of a cavity, such as a cross section of a standard cavity made using known techniques. The shape may be taken or derived from a table of known cavity shapes. Nine known cavity shapes are depicted in FIG. 8. The shape may be a known shape for a traditional waveguide with transformations made.

For example the shape is the two-dimensional cross-section of the periodic structure of a known standard waveguide, similar to what is seen in FIG. 2 or 316, 318 of FIG. 3. Each cavity in iris-to-iris form has a periodic length L (for the repeating accelerating structure), two irises and an equator.

The two-dimensional Cartesian shape may be a longitudinal cross section of a known cavity iris-to-iris. Equally, the two-dimensional Cartesian shape may be a longitudinal cross section of a known cavity equator-to-equator, comprising two equators and one iris. Either unit cell may be used in the method of FIG. 5 since the cavity shape is equivalent for both iris-to-iris and equator-to-equator unit cells.

FIG. 6 shows the longitudinal cross section for a pillbox cavity waveguide, 316, in iris-to-iris form. FIG. 6 is illustrated using an iris-to-iris longitudinal cross section chosen at step 510. This shape is the same as the longitudinal profile 310 reflected in the z axis. The shape—however described—is the two-dimensional longitudinal cross section of the periodic structure of a waveguide cavity. Similarly to FIG. 3, the irises 322 and equators 324 are marked on FIG. 6.

At step 520, the Cartesian two-dimensional cross section of step 510 is converted into polar coordinates (r, θ), the θ direction being defined as between 0 and L/2π to generate a polar cross section. The periodic length of the cell L (the length of the final waveguide cell) is fixed and the geometry of the longitudinal cross section is converted from Cartesian coordinates to a cylindrical coordinate system in the r and θ plane. The θ direction would then be defined as being between 0 and L/2π in terms of this geometry. Step 520 may be executed for a Cartesian two-dimensional cross section of any known cavity shape. Converting the Cartesian two-dimensional cross section into polar coordinates at step 520 is equivalent to mapping the shape onto the r and θ plane. The r and θ plane may be viewed on a polar graph. Conversions to polar coordinates follow the normal equations:

$$r = \sqrt{(x^2+y^2)} \qquad [2]$$

$$\theta = \tan^{-1}(y/x) \qquad [3]$$

A resulting two-dimensional shape, a polar two-dimensional cross section in polar coordinates, is generated. The z axis, the central axis, is in the middle of the two-dimensional polar shape. The polar two-dimensional cross section has no z component. The shape has an order 2 rotational symmetry around the z axis.

For the pillbox cavity shape 316 as shown in FIG. 6, the two-dimensional longitudinal cross section 316 is converted via equations [2] and [3] into polar coordinates (and plotted on a polar graph) to form the polar two-dimensional cross section 610. This is according to step 520 of FIG. 5. The z axis, the central axis 670, is in the middle of the polar two-dimensional cross section 610. The polar two-dimensional cross section has no z component. The shape has an order 2 rotational symmetry around the z axis.

At step 530, the two-dimensional polar cross section of step 520 is helically rotated around the central axis along the length of the cell to generate a hollow 3D shape. The polar two-dimensional cross section is extruded back in the z axis of the Cartesian coordinate system with a twist rate of $\pi/L$. Over a length of L the two-dimensional polar shape is continuously twisted by a total of 180 degrees to generate the 3D shape. The twist rate $\pi/L$ is a fixed rotation rate along the length of the cell L, the twist rate may be defined in units of rad/m or degrees/m. In other implementations different twist rates may be envisaged, however a twist rate of $\pi/L$ provides field cancellation.

The two-dimensional polar cross section is progressively rotated in a continuous fashion around the z axis along the length of the axis, to 'sweep out' the shape of a cavity. This is what is meant by a 'helical rotation' of the shape around the axis. A rotation by 180 degrees over length L results in the three dimensional shape of a cavity. Helical rotation is along length L (a constant), but could also be achieved via variations of this as a continuous function or step function. Since the cross section of the cavity (the two-dimensional polar shape) has a two-degree order of rotational symmetry around the central axis, a rotation of the shape by 180 degrees over the length of the cell means that the transverse cross section of the cavity at the start and the end of the cavity (along the z axis) is the same. In this way multiple cavities can be positioned end-to-end to create a waveguide.

Steps 520 and 530 provide a method for converting a conventional cavity shape into a helical cavity counterpart. In one example steps 520 and 530 may be executed by mapping the cartesian coordinate system onto a helical coordinate system. First a periodic function f(z) in cartesian coordinates is defined, f(z) is representative of the conventional cavity shape (the conventional cavity shape according to step 510) in the z direction. The function f(z) is periodic in terms of the cavity/cell length L along the z axis (the central axis). The function f(z) may define a conventional longitudinal cross section across a plurality of cells. The cartesian function f(z) is then transformed into a new function F($\theta$) in the helical coordinate system, the z values are converted in terms of a twist rate $\pi/L$ and hence the value of a ranges from 0 to L/2$\pi$. The values of $\theta$ are defined by the value of the f(z) function is as the values are converted in the F($\theta$) frame, which can be written:

$$F(\theta) = f\left(\theta \frac{z}{\pi}\right). \qquad [4]$$

At step 540, the three-dimensional shape from step 530 is outputted. The 3D shape is the result of the helical rotation around the z axis. Equivalently, the 3D shape is the result of extrusion in the z axis.

A waveguide having a cavity with the three-dimensional shape is then manufactured. Methods of manufacturing are discussed below in more detail.

FIG. 6—Physical Description of Helical Cavity

FIG. 6 depicts a waveguide having a cavity with a shape derived using the method of FIG. 5. FIG. 6 depicts the two-dimensional polar cross section 610 which has been helically rotated around the z axis form the three-dimensional cavity shape 620. The two-dimensional polar cross section 316 is progressively rotated around the z axis along the length of the axis, to sweep out the shape of a cavity 620. Equivalently, the two-dimensional polar cross section 316 is extruded back in the z axis to form the three-dimensional shape 620.

The 3D shape generated by steps 510 to 540 can be considered a "helical cavity" since the 3D shape defines a resonant cavity and is produced via helical rotation around the z axis. A waveguide which comprises helical cavities may be considered a "helical waveguide". Each helical cavity and helical waveguide have known (non-helical) cavity and waveguide counterparts. For example, helical cavity 620 has a known cavity counterpart 314 which corresponds to an axisymmetric cavity having a longitudinal profile equivalent to the Cartesian 2D cross section used to derive the helical shape.

For a 3D shape (helical cavity) outputted at step 540, any two-dimensional transverse cross-section perpendicular to the z axis (i.e. in the x/y plane) is the same shape as the polar two-dimensional shape of step 520, albeit rotated to a varying degree around the z axis.

However, asymmetry has been introduced in the corresponding x and y longitudinal cross-sections taken along the z axis. In this manner the axisymmetry of the cavity is broken. This is what can be termed as helical rotation along length L (a constant). A helical cavity produced via the method of FIG. 5 can have field-cancelling properties, surface field may be reduced, surface field around the irises may be reduced and RF breakdown may be prevented.

For a 3D shape (helical cavity) outputted at step 540 its transverse cross section (its transverse cross section equivalent to the polar 2D cross section generated at step 520) is continuously helically rotated around the central axis along the length of the cell. The rotational position of the transverse cross sectional shape changes along the length of the cell, the change in rotational position is continuous. The transverse cross section is rotated at a fixed rotation rate along the length of the cell. The fixed rotation rate along the length of the cell can be termed the twist rate, the twist rate may be defined in units of rad/m or degrees/m. In the methods of the present disclosure, the twist rate is defined as $\pi/L$, where L is the length of one cavity (as explained above the length of one cavity L is fixed in the conversation between conventional cavity and helical cavity according to FIG. 5). A twist rate of $\pi/L$ provides 180 degree rotation along the length of the cell.

In the waveguide, the longitudinal cross section corresponds to the two-dimensional Cartesian shape from which the polar transverse cross section was derived. That is, since the 2D polar transverse cross section is helically rotated around the z axis through 180 degrees over the length of the cell, a waveguide cell having a longitudinal cross section in a first longitudinal plane has the two-dimensional Cartesian shape from which the method began. This is the same longitudinal cross section as a cell created using the known method of described above in FIG. 3 of sweeping the longitudinal profile around the z-axis to create an axisymetrical shape. Thus, at one rotational angle around the z-axis, the longitudinal cross section of the helical cell 630 is the same as the longitudinal cross section (at any angle) of the axisymetrical cell 316/318 iris-to-iris (NWN).

At a second rotational angle around the z axis, orthogonal to the first rotational angle, the longitudinal cross section of the helical cell is identical to the cross section of the axisymmetrical cell equator to equator (WNW). In other words, this configuration is such that: at 0 degree cross section (with respect to the z axis) an iris-to-iris unit RF cell (2D cartesian cell shape) is obtained and at a 90 degree cross section (with respect to the z axis) an equator-to-equator unit RF cell (2D cartesian cell shape) is obtained.

Equivalently, the final helical twisted shapes must at cross section taken through the x/z plane along the central axis (i.e. at y=0) produce an iris-to-iris unit RF cell (2D cartesian cell shape), and at cross section through the y/z plane along the central axis (i.e. at x=0) produce an equator-to-equator unit RF cell (2D cartesian cell shape). The x/z and y/z planes are a first and a second plane orthogonal to each other.

A longitudinal cross section can be taken through the helical waveguide cells, where the longitudinal cross section at a first angle around the central axis is an iris-to-iris unit cell and at a second angle around the central axis is an equator-to-equator unit cell, when the first angle is orthogonal to the second angle. The two longitudinal cross sections taken at these two orthogonal angles can be considered as 180 degrees out of phase. This can be seen by example helical cavity 620.

This configuration of the waveguide causes field-cancelling properties.

These conditions for field cancelling properties are illustrated in FIG. 6, the final helical twisted shape 620 viewed over a rotation of 180 degrees with respect to the z axis reproduces an identical cross section in Cartesian coordinates as the helical cavity viewed at a rotation of 0 degrees with respect to the z axis. The cross section viewed at 0 degrees is shown by 630 and at 180 shown by 650. The configuration is such that at 0 degree cross section (with respect to the z axis) an iris-to-iris unit RF cell is obtained and at a 90 degree cross section (with respect to the z axis) an equator-to-equator unit RF cell is obtained. Equivalently, the final helical twisted shape 620 at the longitudinal cross section taken through the x/z plane (i.e. at y=0) produces an iris-to-iris unit RF cell (650) and at longitudinal cross section taken through the y/z plane (i.e. at x=0) produces an equator-to-equator unit RF cell (640).

When the helical cavity 620 is compared to its standard counterpart 314, the helical cavity may reduce surface field, reduce surface field at the irises and improve the accelerating gradient of beam generation its respective waveguide. The standard counterpart 314 is a known (non-helical) cavity which is the starting point from which the helical version 620 is generated.

As explained above, if a longitudinal cross section of the helical cavity 620 is taken at 0 degrees around the z axis, a particular profile 630 is produced, at 90 degrees another profile 640 is produced and at 180 degrees a further profile 650 is produced. In other words, there exists within a particular longitudinal cross-section an analogous phase profile to that described above for the periodicity of iris-to-iris or equator-to-equator features along the length of a conventional known waveguide. However, in the waveguides disclosed herein, a phase can be defined at a particular rotational point around the longitudinal cross-section. Cross sections 630 (iris-to-iris form) and 640 (equator-to-equator form) can be considered the same shape but 180 degrees out of phase (perfectly or exactly out of phase) with each other. This is a condition for a helical cavity to have field cancelling properties. A longitudinal cross section can be taken at any angle around the z axis, and a cross section will be produced that which can be considered the same shape as 630 or 640 just partially out of phase. Any cross section taken around the z axis will have a constant area since the shape is being translated rather than changed. Cross sections 630, 640 and 650 all have the same area contained within the shape.

There is also provided a waveguide which may be referred to as a helical waveguide. A helical waveguide may be produced using the method of FIG. 5, although other methods may be envisaged. A helical waveguide is comprised of helical waveguide cells, the helical waveguide cell comprising a helical cavity. A helical cavity is a cavity comprising a fixed non-circular transverse cross section whose rotational position about the central axis varies along the central axis, such as 620. The central axis of the helical waveguide cell is the acceleration axis for electrons to travel along. The helical waveguide may define a longitudinal cross section in a first plane at a first angle, the waveguide and longitudinal cross section of periodic structure. There may also be defined a longitudinal cross section in a second plane, the second plane orthogonal to the first plane and the periodic structure 180 degrees out of phase relative to the first plane.

For example, the helical cavity 620 may form a helical waveguide cell with central axis 660. A helical waveguide may be comprised of helical waveguide cells, the helical waveguide cells having helical cavities 620. Cavity 620 has a fixed non-circular transverse cross section whose rotational position about the central axis varies along the central axis. The helical waveguide comprised of cavities 620 may define a longitudinal cross section in a first plane at a first angle (630), the waveguide and longitudinal cross section of periodic structure. There may also be defined a longitudinal cross section in a second plane (640), the second plane orthogonal to the first plane and the periodic structure 180 degrees out of phase relative to the first plane.

Any waveguide designed as per the method of FIG. 5 is outputted at step 540, and optionally manufactured at step 550. FIGS. 9a and 9b depict helical cavities as would be manufactured. A waveguide generated in this fashion has the cavities varying as a function of twist, the twist described above as being around the z axis.

After step 540, the method of FIG. 5 may optionally involve simulating the electric field, identifying the maximum field before manufacturing the 3D shape at step 550. These steps are not depicted in the method of FIG. 5. A simulation of the electric field created upon the application of radiofrequency energy to a waveguide comprising cells having the 3D shape, the simulation may be realized via a Maxwell solving computational software, although other simulations may be possible. The simulated electric field created upon the application of radiofrequency energy to a waveguide may also be performed for a cavity having the shape of the two-dimensional Cartesian cross section swept out around the central axis (the known waveguide counterpart, similar to FIG. 3). From these simulations, the maximum surface field can be identified. The maximum surface field for the conventional waveguide may be compared to the maximum surface field for the equivalent helical waveguide.

Each helical cavity has a counterpart (non-helical) cavity produced via known techniques, the known cavity counterpart is the starting point from which the helical version is generated. Each known cavity may have a helical counterpart.

Figure 7:
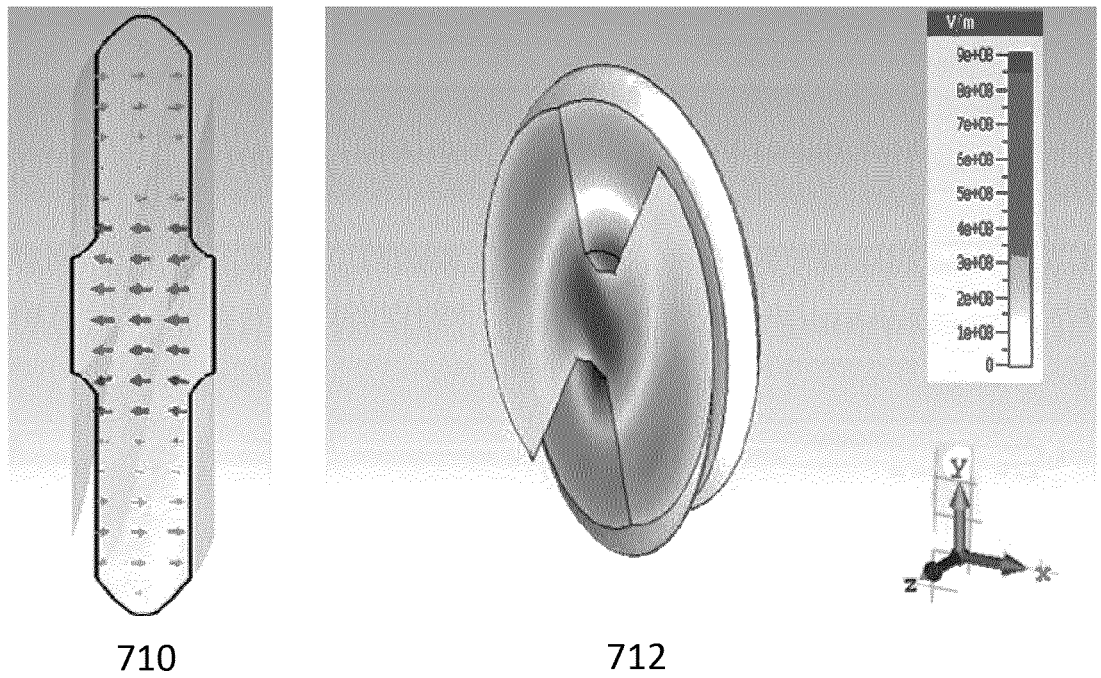
FIG. 7 illustrates a field map formed through the simulated application of RF energy to a helical cavity of the present disclosure.

FIG. 7—Field in a Helical Cavity

FIG. 7 depicts the simulated surface electric field of an example helical cavity 712, the helical cavity produced via the method of FIG. 5 and therefore similar in nature to cavity 620. The original two-dimensional profile received at step 510 to generate helical shape 712 was an Ichiro like shape, the known Ichiro cavity shape is depicted in FIG. 4. A longitudinal cross section of the waveguide cavity 710 (a cross section taken along the z axis) is also depicted.

As with FIGS. 4a and 4b, the intensity is illustrated as a greyscale colour map, with the most intense (i.e. highest density) electric field coloured black, the least intense (i.e. lowest density) field coloured white, and the field intensity therebetween shown in greyscale. The longitudinal cross section 710 additionally contains vector arrows to represent the electric field, the vector arrows coloured according to the greyscale colour map.

It can be seen that the maximum field ratio in the helical cell of FIG. 7 is greatly reduced when compared to the standard cell in FIG. 4. This means that the most intense point of the electric field is along the acceleration path and has moved relative to the point of peak intensity shown in FIG. 4. In the helical cavity 712 of FIG. 7, the point of peak field is not on the surface of the iris; the surface of the iris 410 is no longer coloured black in the plots. The ratio of the intensity of the surface fields have reduced in the helical Ichiro cavity 712 as compared to its standard counterpart shown in FIG. 4b. The standard counterpart of FIG. 4b is the known (non-helical) cavity which is the starting point from which the helical version 712 was generated.

TABLE 1

Simulated comparison between a known waveguide shape and its helical counterpart according to the present disclosure

| Quantity | Conventional "Ichiro" like shape waveguide | Helical "Ichiro" shape cavity waveguide |
| --- | --- | --- |
| R/Q | 138 | 122 |
| Eac(average) MV/m | 500 | 650 |
| Esurf(max) MV/m | 865 | 645 |
| Kilpatrick limit MV/m | 643 | 643 |
| Q(perturbation) | 4900 | 4700 |
| Shunt impedance | 6.5e5 | 5.7e5 |

Further to the results of FIG. 7, Table 1 shows the results of a simulated comparison between a known waveguide Ichiro shape and its helical counterpart according to the present disclosure. The simulated input RF frequency was calculated at 10.9 GHz for both the conventional and helical waveguide shapes. The visual result of this simulation is depicted for the helical waveguide cell in FIG. 7, the conventional waveguide cell visual simulation calculated at 10.9 GHz is not shown. The conventional Ichiro shape waveguide and helical Ichiro shape cavity waveguide have six quantities listed in Table 1: the average accelerating gradient (Eac(average)), the maximum surface electric field (Esurf(max)), the Kilpatrick limit, the quality factor (Q factor), the shunt impedance (R) and the R/Q value.

Table 1 shows that there is a slight reduction in the R/Q, shunt impedance and Q factor of the helical Ichiro shape cavity waveguide, however there is a large reduction on the maximum surface field and an increase in the accelerating gradient for the same simulated stored power (in this instance 1J of energy). Equivalent to the results of FIG. 7, Table 1 shows that surface electric field has reduced, the electric field has moved to along the acceleration path.

The present methods provide a cavity that is optimised in such a way that the most intense electric and magnetic intensities exist only in the path of the accelerated beam, while the fields on all surface structures either do not exist (have been cancelled out) or have been minimised to a level far below the threshold of breakdown. Such a system would have a high accelerating gradient and high quality beam generation. We note that of all possible cell shapes, the above method could only be applied to cavity shapes that are not re-entrant (otherwise a non-manufacturable shape would be obtained, i.e. a shape that geometrically twists back in on itself and self-intersects).

Degenerate Modes (Higher and Lower Order Modes)

In any accelerating structure, other electromagnetic modes can be excited in addition to the desired fundamental mode. These are referred to as higher order modes ("HOMs") or lower order modes ("LOMs"). HOMs and LOMs will create additional electrical and magnetic field variations over and above the desired accelerating electric field. If those variations have a non-trivial component at the acceleration path then they will have an effect on the beam. HOMs and LOMs have an undesired effect on the electron beam. For example, if the higher-order mode has an electrical field component aligned with that of the fundamental mode ($E_z$ along the acceleration path), then the field will vary within an individual cell and may cause the bunch to be spread out.

HOMs and LOMs with electrical fields that run in different directions towards the edges of the cavity ($E_x$ and $E_y$) may cause a lateral force serving to deflect the beam sideways and off the accelerator axis. Thus, it is important to ensure that such higher-order modes are inhibited, especially in applications where a steady and uniform beam is relied upon.

The energy in higher order modes does not contribute to accelerating the charged particle, and therefore the higher order modes result in energy from the rf field being wasted. Eliminating HOMs and/or LOMS provides a more efficient guide in which all of the energy applied to the guide is used in the fundamental field which travels straight down the middle of the cavity and away from the edges.

The helical structures appears to offer field cancellation properties as can be seen in FIG. 7 whereby it appears that the degenerate fields (lower order modes (LOM) and higher order modes (HOM)) typically found in a conventional accelerating equivalent cavity have destructively added together as a result of the rotational twist of the structure. This results in the lowering of the field in regions such that the fields are concentrated only in regions of rotational volume such as the axis and the centres of the side lobes of the structure. A null region is clearly observable just above the iris in the helical structure in FIG. 7 as opposed to that seen in a conventional accelerating structure such as that seen in FIG. 4. The LOM's and HOM's of the helical structure differ significantly as a result as compared to the conventional accelerating equivalent as does the resulting dispersion characteristics, and it is possible with cavity optimisation that other issues and effects caused by such degenerate modes such as the problem of trapped modes could potentially also be minimised using such a structure leading to a much more efficient RF accelerating structure.

FIG. 8 depicts nine different known cavities (cells) by their known longitudinal cross sections (1). A known waveguide comprises the known cavities (cells) of FIG. 8. The known longitudinal cross sections (1) are longitudinal cross sections of known waveguide cells. Each known longitudinal cross section may be used at step 510 of the method of FIG. 5. The known longitudinal cross section is a Cartesian two-dimensional cross section comprising an equator and an iris. Each longitudinal cross section is similar to what is seen in FIG. 2 or 316, 318 of FIG. 3. Each cavity in iris-to-iris form has a periodic length L (for the repeating accelerating structure), two irises and an equator.

There are four standard cavity shapes and five standard cavity shape variants. The four standard cavity shapes are: a pillbox shape, an elliptical shape, an Ichiro shape and a Tesla shape. The shape may be a known shape for a traditional waveguide with transformations made into a variant form. The five standard cavity shapes variants are: a pillbox shape variant 1, a pillbox shape variant 2, a pillbox shape variant 3, a pillbox shape variant 4 and an elliptical shape variant.

For each known cavity (cell) longitudinal cross section, FIG. 8 also depicts the transverse cross section of its corresponding helical cavity (cell). The transverse cross section of the helical cavity is a polar coordinate conversion of the longitudinal cross section of a standard cavity, where the known cavity has been converted into its helical cavity counterpart according to the methods of the present disclosure, FIG. 5. The helical cavity (cell) for each known cavity shape is shown in FIG. 8, each helical cell generated according to the method of FIG. 5.

The skilled person will appreciate that other shapes may be used to produce a waveguide according to the present disclosure.

As explained above, a helical cavity has a longitudinal cross section a first plane and the longitudinal cross section in a second plane orthogonal to the first plane that are the same shape but 180 degrees out of phase relative to each other (perfectly out of phase). This provides field cancelling properties.

For instance the longitudinal cross section of the cell viewed in a first plane may be the iris-to-iris 2D cartesian cell shape, and viewed in a second plane orthogonal to the first plane may be the equator-to-equator 2D cartesian cell shape.

FIG. 8 depicts two longitudinal cross sections for each of the nine depicted helical cavity shapes. A first longitudinal cross section taken at first plane (the x/z plane at y=0) through each 3D helical cell and a second longitudinal cross section taken at second place (the y/z plane at x=0) through each 3D helical cell. The first and the second planes are orthogonal to each other. Each of the nine helical waveguide cells depicted in FIG. 8 display field cancelling properties since at the first plane an iris-to-iris unit RF cell (2D cartesian cell shape) is obtained and at a second plane an equator-to-equator unit RF cell (2D cartesian cell shape) is obtained. Equivalently, for each of the nine helical cavities at 0 degree cross section (with respect to the z axis) an iris-to-iris unit RF cell (2D cartesian cell shape) is obtained and at a 90 degree cross section (with respect to the z axis) an equator-to-equator unit RF cell (2D cartesian cell shape) is obtained. It can be see from FIG. 8 that the longitudinal cross section of the helical cell through the second plane (the y/z plane) is an equator to equator until which is the same shape as the known waveguide cell longitudinal cross section.

The longitudinal cross section of the helical cavity ('helical longitudinal cross section') has the same shape as the longitudinal cross section of the standard counterpart cavity ('known waveguide cell longitudinal cross section') from which the helical cavity was derived. The helical longitudinal cross section corresponds to the known waveguide cell longitudinal cross section at a different point along the length of the known waveguide cavity depending on the angle of the plane of the helical longitudinal cross section. That is, the helical longitudinal cross section is the known waveguide cell longitudinal cross section translated by a certain amount along the cell length. As the angle of the plane of the helical longitudinal cross section varies around the z axis, the amount of translation of the known waveguide cell longitudinal cross section changes. The cross section is a cell shape taken from a different point along the length of the cell. Viewing the helical longitudinal cross section in a plane continuously rotated about the z axis corresponds to the known waveguide cell cross section continuously translated along the z axis. Rotation of the helical longitudinal cross section by 90 degrees around the z axis corresponds to translation of a known waveguide cell longitudinal cross section by half a cell length along the z axis.

FIG. 9—Manufacturing Options

FIG. 9 depicts a helical cavity of the present disclosure 910 and two corresponding three-dimensional shapes which may be used to manufacture a waveguide comprising helical cavities 910. FIG. 9 shows two shapes, 920, 930, corresponding to two different methods of manufacture for a waveguide comprising helical cavities 910. The methods of manufacture may be used in step 550 of FIG. 5. The manufacture shapes may be designed or imported into CAD software. The helical cavities may be manufactured into a waveguide, the waveguide for use in a linear accelerator and/or in a radiotherapy device.

Traditionally, cavities are each individually manufactured from a conductive metal such as copper, the cavities are then stacked adjacently to form a waveguide. The cavities may be joined via brazing or welding, using segments of conductive material together at joining portions. The joining portions of the segments are typically in the equator of the cavity.

Some helical cavities of the present disclosure, such as 910, may be manufactured using traditional methods. For example, 920 is an individual cavity which may be repeatedly manufactured, the individual pieces may be welded together at joining portions to form a waveguide. The helical cavity 910 was generated by the method of FIG. 5, the identified Cartesian two-dimensional cross section at step 510 was an Ichiro shape. For helical cavity 910, the simplest repeating unit to manufacture is the shape 920 which is half the length of helical cavity 910. As previously defined, length of a cavity refers to its distance along the central axis (z axis). The shape 920 is effectively what is "printed" into a component piece. To form one helical cavity 910, two pieces 920 may be stacked at 90 degrees to each other. Of course, to form a waveguide many pieces such as 920 may be stacked each at 90 degrees to each other, a many cavities are needed to form a waveguide. Other waveguides comprising helical cavities according to present disclosure may be similarly manufactured using half helical cavities as the repeating unit. Alternatively, for other waveguides comprising helical cavities according to present disclosure, these waveguides may be manufactured using entire helical cavities as the repeating unit. The choice of repeating unit depends on which repeating unit is easiest to manufacture and which repeating unit will be easiest to join to form the waveguide.

Alternatively, cavities may be manufactured into a waveguide using a split or "subway sandwich" technique. In this technique, a plurality of cavities are rendered virtually, for example in CAD software. The plurality of cavities may form a segment of the waveguide, or in some cases the entire waveguide. The waveguide segment is cut along the acceleration axis which is equivalent to cutting through a longitudinal plane (for example the y/z or x/z plane) to form two halves. The two halves are manufactured as two component pieces, the two halves "sandwich" to form the waveguide segment. The two halves are "sandwiched" together by welding. The process may be repeated for the number of waveguide segments which form the entirety waveguide. The waveguide segments may be joined together to form the entire waveguide via welding.

This disclosure also relates to a method of manufacturing a waveguide of the present disclosure.

Some helical cavities of the present disclosure may be manufactured using the subway sandwich method. In particular, for more complex geometries, the subway sandwich technique may be easier and more successful to implement than traditional methods. For example, one half of waveguide segment 930 for the subway sandwich manufacturing technique is depicted in FIG. 9, the other half of the waveguide segment is not shown. The half depicted in FIG. 9 is manufactured as one component piece along with the corresponding other half as a second, separate component piece. The two halves are sandwiched together via welding to form a waveguide segment. A plurality of waveguide segments are made in this fashion, the waveguide segments welded together to form a entire waveguide. The helical cavity manufacture shape 930 originates from helical cavity shape 910 generated by the methods of FIG. 5. Two and a half cavities 910 comprise the waveguide segment 930.

Cavities in a waveguide may vary in shape, waveguide manufacture may involve making slight changes to the cavity shape according to the location of the cavity in the waveguide. For example, cavities nearer the electron gun may be used for bunching of electrons and may be shorter in length when compared to cavities nearer the heavy-metal target used for acceleration.

Advantages

Designing a waveguide according to the present disclosure, the dimensions of the waveguide are not limited by creating a sweep of a two-dimensional model around the central axis. Instead, a three-dimensional model of the waveguide is created in which the dimensions of the cavity vary around the axis. Therefore, the crosswise cross section of the acceleration channel at a point is not circular or toroidal. This is a radical departure from the waveguides comprised in the prior art.

The helical waveguide of the present invention has field cancelling properties. When a helical cavity is compared to its known counterpart, the helical cavity may reduce surface field, reduce surface field at the irises and improve the accelerating gradient of beam generation its respective waveguide. As explained above, a high electric field at the surface of a cavity can cause RF breakdown at these locations. Whether RF breakdown occurs can be somewhat predicted by empirically derived formulas such as the Kilpatrick breakdown limit. If the surface field is greater than the Kilpatrick breakdown limit, there is high probability of RF breakdown in this location. The Kilpatrick limit provides an estimate since the mechanism of RF breakdown does depends on many factors such as field emissions, multipacting, gas breakdown and surface heating.

When the Kilpatrick limit test is applied to the helical cavities of the present disclosure, the surface field is approximately the same as the limit which predicts there will not be RF breakdown at these locations. Additionally, if the surface field is reduced to below the threshold for RF breakdown, the input RF frequency can be safely increased without causing RF breakdown. Increasing the applied RF energy increases the intensity of the field throughout the waveguide, including the field on the acceleration path. Thus more energy can be delivered to the electrons, the x-ray beam can be of a higher energy and patient treatment times may be reduced.

With reference to Table 1, the Kilpatrick limit was 643 (MV/m) for both the conventional Ichiro shape waveguide and the helical Ichiro shape cavity waveguide since the input frequency was the same for both (10.9 GHz). For the conventional waveguide the maximum electric field was 865 MV/m which is above the Kilpatrick limit (643 MV/m) and implies that, at this frequency, there would be RF breakdown and the conventional waveguide would be unable to operate at this frequency level. However, for the helical waveguide, the maximum electric field was 645 MV/m which is approximately equal to the Kilpatrick limit (643 MV/m) which implies no RF breakdown at this frequency level.

The location of the maximum surface field in accelerating structures, normal conducting or superconducting, is typically found on the iris of the cells as this is where the surface field is most concentrated due to the geometry and the way the fields interact with the surface. However, in alternative designs such as the helical geometry proposed in the present disclosure, the maximum surface field may be either greatly reduced in these regions of shifted to a new location. The field created in a cavity may be minimised at all or some locations aside from along the acceleration path. A reduction of the maximum surface field whether this be localised to a point or across a surface will lead to a structure that may produce a higher accelerating gradient. An example increase of the acceleration gradient for a helical cavity waveguide in comparison to its conventional counterpart can be seen in Table 1.

A further factor which affects breakdown is the roughness of the surface. A smoother surface is less likely to cause breakdown than a rough surface. That is, increased roughness of the edge of the cavity increases the likelihood of breakdown. The iris is the most difficult portion of the cavity to machine to a high smoothness. By moving the point of peak field away from the surface or by reducing the field at the iris, a rougher surfaced cavity can be used without causing breakdown. Alternatively, or additionally, a higher accelerating field can be used without causing breakdown.

Moving the field away from the iris means that the level of smoothness and uniformity at the nose cone or iris can be reduced whilst maintaining the accelerating ability and efficiency of the waveguide. Again, this is because the effect of having a helical cavity waveguide is that the highest intensity part of the electric field is reduced at the surface. Since the iris is difficult to manufacture and particularly difficult to smooth, this will reduce the cost of manufacturing a waveguide without reducing the dose rate achievable by the waveguide.

An additional advantage is that, if the fields are reduced at the surface, it could be possible to weld cells together in a plane in which the acceleration path lies. This means that to manufacture a waveguide, many cavities could be made at once, using two opposing halves welded together as in the subway sandwich approach depicted by FIG. 9b. This technique is not currently possible without intensely accurate positioning of the two halves, since if surface fields are present the cavities and slight misalignment would have a huge impact on the electric field created in the waveguide.

As explained above, the helical cavities offer field cancellation properties as can be seen in FIG. 7 whereby it appears that the degenerate fields (lower order modes (LOM) and higher order modes (HOM)) typically found in a conventional accelerating equivalent cavity have destructively added together as a result of the rotational twist of the structure. This results in the lowering of the field in regions such that the fields are concentrated only in regions of rotational volume such as the axis and the centres of the side lobes of the structure. A null region is clearly observable just above the iris in the helical structure in FIG. 7 as opposed to that seen in a conventional accelerating structure such as that seen in FIG. 4. The LOM's and HOM's of the helical structure differ significantly as a result as compared to the conventional accelerating equivalent as does the resulting dispersion characteristics, and it is possible with cavity optimisation that other issues and effects caused by such degenerate modes such as the problem of trapped modes could potentially also be minimised using such a structure leading to a much more efficient RF accelerating structure In summary there is provided a waveguide comprising helical cavities, the shape of which advantageously reduces surface fields.

Variants

Throughout the present disclosure, reference is made to reduction in surface fields, in particular electric field. However, a reduction in surface field can equally refer to magnetic fields according to the present invention. Magnetic fields have not been illustrated for the sake of simplicity.

Once a waveguide has been produced, the waveguide may be "tuned" to try to reduce asymmetry in the field created in the waveguide. This can be done by taking a measurement of the electric field created in a waveguide upon the application of radiofrequency energy, introducing a dent into the waveguide, and then taking another measurement of the electric field to determine whether the asymmetry has been reduced. The overall aim of known tuning is to reduce asymmetry across the board to align the optimum path the electrons take.

There are multiple methods of waveguide tuning. The first is to using tuning dents or studs on the equator locations on the 0 or 90 degree cross-sectional positions (with respect the z axis), this introduces a volume change and a frequency shift and this is applicable to any of the helical cavities of the present disclosure. If the structure has a thin enough iris section, for example seen in the Ichiro shape, then it may be possible to adjust the length of the unit cell by pulling the iris using a special tool at either the 0 or 90 degree cross-sectional positions, this adjusts the twist of the cell and has a larger effect of the phase and a smaller effect on the frequency shift. Dielectrically loading the structures with an RF absorber, such as SiC at the 0 or 90 degree cross-sectional positions, can introduce a frequency shift. Precision machining the structures can be done such that the structures do not require tuning either after brazing (if this is the preferred method of manufacture) or from older manufacturing techniques such as electroforming (and either removal of the inner die via dissolving in acid or by growing the surface on a pre-existing die).

The modes within the helical cavity may be considered to be hybrid modes rather than pure transverse electric modes (TE) or transverse magnetic modes (TM) seen in conventional RF cavities. When using the same geometric inputs the obtained frequency in a helical cavity may be higher than that of its conventional counterpart and this needs to be compensated for by a slight increase in the height of the cavity. The height of the helical cavity may be increased by a trial and error method until the RF frequencies of helical and conventional cavity match. It is not always necessary to reproduce the same frequency in a helical cavity as in its conventional counterpart. Indeed one of the advantages of the present invention is to provide a system where higher frequencies of RF may be safely used without experiencing breakdown.

Therefore the method described above may include an additional step of adjusting the height of the helical cavity. This is done after the step of 540 in the method of FIG. 5. The electric field over time generated by the application of radiofrequency waves to the waveguide is simulated. The RF frequency generated in the helical cell is compared to the RF frequency induced when RF energy is applied to a standard waveguide (an axisymmetric waveguide having a cavity with the longitudinal cross section equivalent to the 2D cartesian shape in step 510 of the method). The frequency in the helical cavity is compared to the frequency in the conventional cavity. If the frequency is different, or are not within a threshold value of one another, the height of the helical cavity is increased to create a modified helical cavity shape. The electric field over time generated by application of RF waves to the modified helical cavity is simulated. The frequency in the modified helical cavity is compared to the frequency in the conventional cavity. If the frequencies do not match, the helical cavity shape is modified again and the method is repeated. If the frequencies match, or are within a threshold value of one another, the helical shape is outputted as the final shape.

Thus far the acceleration of electrons has referred to on axis acceleration, but is also possible to support deflecting modes generated in the helical cavities for acceleration. Deflecting modes have different applications to axis acceleration. Axis acceleration may be used in a linear accelerator for radiotherapy device, deflecting modes may be used for particle separation and temporal beam diagnostics. If the ratio of length to height of the equator remains below a certain ratio for any of the described helical cavities, on axis acceleration is obtained. At some point the ratio is exceeded (i.e. if the cavity is made very long) and then the field cancellation of the helical cavities results in deflecting modes rather than on axis accelerating modes. Deflecting modes result in a complicated to machine accelerating structure. It may only be possible to manufacture such an arrangement using deflecting modes for these types of shapes by the subway sandwich approach, similar to 930 of FIG. 9. It is possible to put a beam pipe in along the axis for the deflecting mode cavities without too much perturbation to the system (i.e. field cancellation still occurs).

The helical waveguide of the present invention comprising helical waveguide cells (helical cavities) may be used in a standing wave configuration or in a travelling wave configuration. Helical waveguides are also applicable to both high and low beta cavity configurations. Any type of charged particle may be accelerated in a helical waveguide, for example electrons, proton, or ions (carbon or otherwise).

As well as providing a waveguide cell and a waveguide according to the above description, this disclosure also relates to a particle accelerator comprising the disclosed waveguide, and to a linear accelerator comprising the disclosed waveguide. There is also disclosed a radiotherapy device comprising the linear accelerator.

There is also disclosed a method of manufacturing the waveguide described herein.

Definitions

Axisasymmetry

In an asymmetric waveguide according to the present disclosure, the walls defining the edge of the cavity do not remain a constant distance from the central axis in a rotation around the axis. That is, the transverse cross-section of the acceleration cavity at a given point is not circular. The radius defining the distance from the walls to the central axis is not constant around the central axis; it instead varies through rotation around the central axis. In other words, the order of rotational symmetry of the transverse cross section of the acceleration channel around the central axis is not infinite; it is discrete.

The waveguide described above can be used in a particle accelerator. The particle accelerator may be a linear accelerator. The linear accelerator may be used in a radiotherapy device.

The waveguide is manufactured through: manufacturing a series of cavities interconnected along a central axis to form an acceleration channel. In a specific embodiment, manufacturing a series of cavities comprises manufacturing a plurality of segments of material defining a portion of at least one cavity; and joining the segments to form the series of interconnected cavities. The material can be any conducting material, and in a specific embodiment is copper. The segments are joined through brazing or welding. The manufactured waveguide can have any of the properties or dimensions of the waveguide of the present disclosure as described above.

There is also provided a waveguide manufactured using the disclosed method.

Accelerating Cavity

Accelerating cavities are cavities through which the acceleration path passes.

An additional member inserted into an acceleration channel, for example a coupler projecting into the acceleration path, does not affect the shape of the acceleration channel or of the accelerating cavity. The acceleration cavity, and the shape of the acceleration cavity, is intended to mean the shape enclosing the volume of the channel through which the acceleration path of the electron passes.

Features of the above aspects can be combined in any suitable manner. It will be understood that the above description is of specific embodiments by way of aspect only and that many modifications and alterations will be within the skilled person's reach and are intended to be covered by the scope of the appendant claims.

The invention claimed is:

1. A waveguide cell comprising:
a helical cavity; and
a central axis, wherein the helical cavity includes a transverse cross section whose rotational position about the central axis varies along the central axis, wherein a longitudinal cross section of the waveguide cell in a first plane and a longitudinal cross section of the waveguide cell in a second plane, orthogonal to the first plane, are a same shape 180 degrees out of phase relative to each other, wherein the transverse cross section is a polar coordinates conversion of an iris-to-iris 2D cartesian cell shape, and wherein the longitudinal cross section of the waveguide cell viewed in a first plane is the iris-to-iris 2D cartesian cell shape, and wherein the longitudinal cross section of the waveguide cell viewed in a second plane, orthogonal to the first plane is an equator-to-equator 2D cartesian cell shape.

2. The waveguide cell of claim 1, wherein the transverse cross section is continuously helically rotated along a length of the waveguide cell.

3. The waveguide cell of claim 2, wherein the transverse cross section is rotated at a fixed rotation rate along the length of the waveguide cell.

4. The waveguide cell of claim 2, wherein the transverse cross section is helically rotated along the length of the waveguide cell through at least 180 degrees.

5. The waveguide cell of claim 1, in combination with one or more additional waveguide cells in a series arrangement.

6. The waveguide cell of claim 1, wherein the longitudinal cross section in the first plane has a periodic structure, and wherein the longitudinal cross section in the second plane has the periodic structure 180 degrees out of phase relative to the first plane.

7. A method of generating a three-dimensional (3D) shape of a waveguide cell, the method comprising:
identifying a two-dimensional (2D) cross section of the waveguide cell, wherein identifying a 2D cross section comprises:
identifying a Cartesian 2D cross section of the waveguide cell in Cartesian coordinates; and
generating a polar 2D cross section in polar coordinates by converting the 2D Cartesian cross section into polar coordinates defining a $\theta$ direction between 0 and $L/2\pi$;
helically rotating the (2D) cross section around a central axis along a length (L) of the waveguide cell to generate a 3D shape, wherein helically rotating the 2D cross section around the central axis along the length of the cell to generate a 3D shape comprises:
extruding the 2D polar coordinates shape back in a z axis of the Cartesian coordinate system with a twist rate of $\pi/L$; and
outputting the 3D shape.

8. The method of claim 7 wherein helically rotating the cross section comprises rotating the cross section along the length of the waveguide cell through 180 degrees.

9. The method of claim 7, wherein identifying a 2D cross section comprises:
identifying a periodic Cartesian 2D cross section of the waveguide cell, wherein the periodic Cartesian 2D cross section defines a periodic function f(z);
and wherein helically rotating the cross section around the central axis along the length of the waveguide cell to generate a 3D shape comprises:
transforming the periodic function f(z) into a new function $F(\theta)$ in a helical coordinate system, wherein one or more z values are converted by a twist rate $\pi/L$ and a value of $\theta$ ranges from 0 to $L/2\pi$.

10. The method of claim 7, wherein the Cartesian 2D cross section of the cell comprises an iris-to-iris cell shape, and wherein a longitudinal cross section of the waveguide cell in a first plane is the iris-to-iris Cartesian cell shape, and in a second plane, orthogonal to the first plane, is an equator-to-equator Cartesian cell shape.

11. The method of claim 10, wherein the Cartesian 2D cross section is the longitudinal cross section of a known cavity shape and wherein the known cavity shape comprises one of:
a pillbox shape, an elliptical shape, an Ichiro shape or a Tesla shape.

12. A linear accelerator comprising:
a waveguide, the waveguide including:
a waveguide cell, the waveguide cell including:
a central axis; and
a helical cavity, wherein the helical cavity includes a transverse cross section, wherein a rotational position of the transverse cross section about the central axis varies along the central axis, wherein a longitudinal cross section of the waveguide cell in a first plane and a longitudinal cross section of the waveguide cell in a second plane, orthogonal to the first plane, are a same shape 180 degrees out of phase relative to each other, wherein the transverse cross section is a polar coordinates conversion of an iris-to-iris 2D cartesian cell shape, and wherein the longitudinal cross section of the waveguide cell viewed in a first plane is the iris-to-iris 2D cartesian cell shape, and wherein the longitudinal cross section of the waveguide cell viewed in a second plane, orthogonal to the first plane, is an equator-to-equator 2D cartesian cell shape.

13. The linear accelerator of claim 12, wherein the transverse cross section is continuously helically rotated along a length of the waveguide cell.

14. The linear accelerator of claim 13, wherein the transverse cross section is rotated at a fixed rate of rotation along the length of the waveguide cell, and wherein the transverse cross section is helically rotated along the length of the waveguide cell through 180 degrees.

\* \* \* \* \*